United States Patent
Lee et al.

(10) Patent No.: US 9,351,658 B2
(45) Date of Patent: May 31, 2016

(54) DEVICE AND METHOD FOR SENSING ELECTRICAL ACTIVITY IN TISSUE

(75) Inventors: Michael J. Lee, Carmel, CA (US); Hans C. Lee, Carmel, CA (US)

(73) Assignee: The Nielsen Company (US), LLC, Schaumburg, IL (US)

(*) Notice: Subject to any disclaimer, the term of this patent is extended or adjusted under 35 U.S.C. 154(b) by 86 days.

(21) Appl. No.: 11/500,678

(22) Filed: Aug. 8, 2006

(65) Prior Publication Data

US 2007/0055169 A1  Mar. 8, 2007

Related U.S. Application Data

(60) Provisional application No. 60/713,899, filed on Sep. 2, 2005.

(51) Int. Cl.
*A61B 5/0476* (2006.01)
*A61B 5/04* (2006.01)
*A61B 5/048* (2006.01)
*A61B 5/00* (2006.01)

(52) U.S. Cl.
CPC ............. *A61B 5/0476* (2013.01); *A61B 5/0006* (2013.01); *A61B 5/048* (2013.01); *A61B 5/6814* (2013.01); *A61B 5/0002* (2013.01)

(58) Field of Classification Search
CPC .... A61B 5/0476; A61B 5/0478; A61B 5/048; A61B 5/0482; A61B 5/0484
USPC ........................... 600/544, 545, 546; 128/925
See application file for complete search history.

(56) References Cited

U.S. PATENT DOCUMENTS

| | | | |
|---|---|---|---|
| 4,695,879 A | 9/1987 | Weinblatt | |
| 4,755,045 A | 7/1988 | Borah et al. | |
| 4,846,190 A * | 7/1989 | John | 600/544 |
| 4,931,934 A | 6/1990 | Snyder | |
| 4,974,602 A | 12/1990 | Abraham-Fuchs et al. | |
| 5,024,235 A * | 6/1991 | Ayers | 600/545 |
| 5,243,517 A | 9/1993 | Schmidt et al. | |
| 5,406,957 A | 4/1995 | Tansey | |
| 5,447,166 A | 9/1995 | Gevins | |
| 5,450,855 A | 9/1995 | Rosenfeld | |
| 5,513,649 A | 5/1996 | Gevins et al. | |
| 5,579,774 A | 12/1996 | Miller et al. | |

(Continued)

FOREIGN PATENT DOCUMENTS

| | | |
|---|---|---|
| EP | 1052582 | 11/2000 |
| EP | 1389012 | 2/2004 |

(Continued)

OTHER PUBLICATIONS

Egner, Tobias; Emilie Strawson, and John H Gruzelier. "EEG Signture and Phenomenology of Alpha/theta Neurofeedback Training Versus Mock Feedback." Applied Psychophysiology and Biofeedback. vol. 27, No. 4. Dec. 2002.*

(Continued)

*Primary Examiner* — Adam J Eiseman
(74) *Attorney, Agent, or Firm* — Hanley, Flight & Zimmerman, LLC

(57) ABSTRACT

An exemplary embodiment providing one or more improvements includes apparatus and methods for sensing electrical activity in tissue of a person in a manner which is substantially limits or eliminates interference from noise in a surrounding environment.

41 Claims, 7 Drawing Sheets

(56) References Cited

U.S. PATENT DOCUMENTS

| | | |
|---|---|---|
| 5,601,090 A | 2/1997 | Musha |
| 5,649,061 A | 7/1997 | Smyth |
| 5,676,138 A | 10/1997 | Zawilinski |
| 5,692,906 A | 12/1997 | Corder |
| 5,724,987 A | 3/1998 | Gevins et al. |
| 5,740,812 A | 4/1998 | Cowan |
| 5,774,591 A | 6/1998 | Black et al. |
| 5,983,129 A | 11/1999 | Cowan et al. |
| 5,983,214 A | 11/1999 | Lang et al. |
| 5,995,868 A | 11/1999 | Dorfmeister et al. |
| 6,001,065 A | 12/1999 | DeVito |
| 6,016,444 A | 1/2000 | John |
| 6,099,319 A | 8/2000 | Zaltman et al. |
| 6,117,092 A | 9/2000 | Weinstein et al. |
| 6,254,536 B1 | 7/2001 | DeVito |
| 6,259,889 B1 | 7/2001 | LaDue |
| 6,270,466 B1 | 8/2001 | Weinstein et al. |
| 6,292,688 B1 | 9/2001 | Patton |
| 6,309,342 B1 | 10/2001 | Blazey et al. |
| 6,322,368 B1 | 11/2001 | Young et al. |
| 6,349,231 B1 | 2/2002 | Musha |
| 6,422,999 B1 | 7/2002 | Hill |
| 6,425,764 B1 | 7/2002 | Lamson |
| 6,434,419 B1 | 8/2002 | Gevins et al. |
| 6,453,194 B1 | 9/2002 | Hill |
| 6,481,013 B1 | 11/2002 | Dinwiddie et al. |
| 6,520,905 B1 * | 2/2003 | Surve et al. ............. 600/26 |
| 6,585,521 B1 | 7/2003 | Obrador |
| 6,606,102 B1 | 8/2003 | Odom |
| 6,609,024 B1 | 8/2003 | Ryu et al. |
| 6,623,428 B2 | 9/2003 | Miller et al. |
| 6,626,676 B2 | 9/2003 | Freer |
| 6,648,822 B2 | 11/2003 | Hamamoto et al. |
| 6,652,283 B1 | 11/2003 | Van Schaack et al. |
| 6,656,116 B2 | 12/2003 | Kim et al. |
| 6,678,866 B1 | 1/2004 | Sugimoto et al. |
| 6,699,188 B2 | 3/2004 | Wessel |
| 6,792,304 B1 | 9/2004 | Silberstein |
| 6,839,682 B1 | 1/2005 | Blume |
| 6,978,115 B2 | 12/2005 | Whitehurst et al. |
| 7,035,685 B2 * | 4/2006 | Ryu et al. ............. 600/544 |
| 7,050,753 B2 | 5/2006 | Knutson |
| 7,113,916 B1 | 9/2006 | Hill |
| 7,127,283 B2 | 10/2006 | Kageyama |
| 7,194,186 B1 | 3/2007 | Strub et al. |
| 7,246,081 B2 | 7/2007 | Hill |
| D565,735 S | 4/2008 | Washbon |
| 7,383,728 B2 | 6/2008 | Noble et al. |
| 7,627,880 B2 | 12/2009 | Itakura |
| 7,630,757 B2 | 12/2009 | Dorfmeister et al. |
| 7,689,272 B2 | 3/2010 | Farwell |
| 7,716,697 B2 | 5/2010 | Morikawa et al. |
| 7,739,140 B2 | 6/2010 | Vinson et al. |
| 7,742,623 B1 | 6/2010 | Moon et al. |
| 7,751,878 B1 | 7/2010 | Merkle et al. |
| 7,805,009 B2 | 9/2010 | Everett et al. |
| 7,853,122 B2 | 12/2010 | Miura et al. |
| 7,930,199 B1 | 4/2011 | Hill |
| 7,942,816 B2 | 5/2011 | Satoh et al. |
| 8,235,725 B1 | 8/2012 | Hill |
| 8,326,002 B2 | 12/2012 | Hill |
| 8,600,100 B2 | 12/2013 | Hill |
| 2001/0016874 A1 | 8/2001 | Ono et al. |
| 2001/0056225 A1 | 12/2001 | DeVito |
| 2002/0103429 A1 | 8/2002 | deCharms |
| 2002/0107454 A1 | 8/2002 | Collura et al. |
| 2002/0154833 A1 | 10/2002 | Koch et al. |
| 2002/0182574 A1 | 12/2002 | Freer |
| 2002/0188216 A1 * | 12/2002 | Kayyali et al. ............. 600/544 |
| 2003/0003433 A1 | 1/2003 | Carpenter et al. |
| 2003/0055355 A1 | 3/2003 | Viertio-Oja |
| 2003/0063780 A1 | 4/2003 | Gutta et al. |
| 2003/0066071 A1 | 4/2003 | Gutta et al. |
| 2003/0067486 A1 | 4/2003 | Lee et al. |
| 2003/0076369 A1 | 4/2003 | Resner |
| 2003/0081834 A1 | 5/2003 | Philomin et al. |
| 2003/0093784 A1 | 5/2003 | Dimitrova et al. |
| 2003/0126593 A1 | 7/2003 | Mault |
| 2003/0153841 A1 | 8/2003 | Kilborn et al. |
| 2004/0013398 A1 | 1/2004 | Miura et al. |
| 2004/0018476 A1 | 1/2004 | Ladue |
| 2004/0039268 A1 | 2/2004 | Barbour et al. |
| 2004/0072133 A1 | 4/2004 | Kullock et al. |
| 2004/0077934 A1 | 4/2004 | Massad |
| 2004/0088289 A1 | 5/2004 | Xu et al. |
| 2004/0111033 A1 | 6/2004 | Oung et al. |
| 2004/0161730 A1 | 8/2004 | Urman |
| 2004/0193068 A1 | 9/2004 | Burton et al. |
| 2004/0208496 A1 | 10/2004 | Pilu |
| 2004/0267141 A1 | 12/2004 | Amano et al. |
| 2005/0010087 A1 | 1/2005 | Banet et al. |
| 2005/0010116 A1 | 1/2005 | Korhonen et al. |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 | 3/2005 | Martins |
| 2005/0096311 A1 | 5/2005 | Suffin et al. |
| 2005/0097594 A1 | 5/2005 | O'Donnell et al. |
| 2005/0113656 A1 | 5/2005 | Chance |
| 2005/0120372 A1 | 6/2005 | Itakura |
| 2005/0143629 A1 | 6/2005 | Farwell |
| 2005/0165285 A1 | 7/2005 | Iliff |
| 2005/0172311 A1 | 8/2005 | Hjelt et al. |
| 2005/0223237 A1 | 10/2005 | Barletta et al. |
| 2005/0289582 A1 | 12/2005 | Tavares et al. |
| 2006/0010470 A1 | 1/2006 | Kurosaki et al. |
| 2006/0064037 A1 | 3/2006 | Shalon et al. |
| 2006/0094970 A1 | 5/2006 | Drew |
| 2006/0111621 A1 | 5/2006 | Coppi et al. |
| 2006/0143647 A1 | 6/2006 | Bill |
| 2006/0217598 A1 | 9/2006 | Miyajima et al. |
| 2006/0258926 A1 | 11/2006 | Ali et al. |
| 2006/0265022 A1 | 11/2006 | John et al. |
| 2006/0277102 A1 | 12/2006 | Agliozzo |
| 2006/0293608 A1 * | 12/2006 | Rothman et al. ............. 600/545 |
| 2006/0293921 A1 | 12/2006 | McCarthy et al. |
| 2007/0031798 A1 | 2/2007 | Gottfried |
| 2007/0048707 A1 | 3/2007 | Caamano et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066914 A1 | 3/2007 | Le et al. |
| 2007/0116037 A1 | 5/2007 | Moore |
| 2007/0168461 A1 | 7/2007 | Moore |
| 2007/0173733 A1 | 7/2007 | Le et al. |
| 2007/0179396 A1 | 8/2007 | Le et al. |
| 2007/0184420 A1 | 8/2007 | Mathan et al. |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0249952 A1 | 10/2007 | Rubin et al. |
| 2007/0265507 A1 | 11/2007 | De Lemos |
| 2008/0039737 A1 | 2/2008 | Breiter et al. |
| 2008/0091512 A1 | 4/2008 | Marci et al. |
| 2008/0144882 A1 | 6/2008 | Leinbach et al. |
| 2008/0159365 A1 | 7/2008 | Dubocanin et al. |
| 2008/0161651 A1 | 7/2008 | Peterson et al. |
| 2008/0162182 A1 | 7/2008 | Cazares et al. |
| 2008/0177197 A1 | 7/2008 | Lee et al. |
| 2008/0201731 A1 | 8/2008 | Howcroft |
| 2008/0211768 A1 | 9/2008 | Breen et al. |
| 2008/0218472 A1 | 9/2008 | Breen et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030930 A1 | 1/2009 | Pradeep et al. |
| 2009/0036755 A1 | 2/2009 | Pradeep et al. |

(56) References Cited

U.S. PATENT DOCUMENTS

| | | | |
|---|---|---|---|
| 2009/0036756 | A1 | 2/2009 | Pradeep et al. |
| 2009/0062629 | A1 | 3/2009 | Pradeep et al. |
| 2009/0062681 | A1 | 3/2009 | Pradeep et al. |
| 2009/0063255 | A1 | 3/2009 | Pradeep et al. |
| 2009/0063256 | A1 | 3/2009 | Pradeep et al. |
| 2009/0082643 | A1 | 3/2009 | Pradeep et al. |
| 2009/0083129 | A1 | 3/2009 | Pradeep et al. |
| 2009/0105576 | A1 | 4/2009 | Do et al. |
| 2009/0112077 | A1 | 4/2009 | Nguyen et al. |
| 2009/0156907 | A1 | 6/2009 | Jung et al. |
| 2009/0156925 | A1 | 6/2009 | Jin et al. |
| 2009/0156955 | A1 | 6/2009 | Jung et al. |
| 2009/0163777 | A1 | 6/2009 | Jung et al. |
| 2009/0171164 | A1 | 7/2009 | Jung et al. |
| 2009/0214060 | A1 | 8/2009 | Chuang et al. |
| 2009/0222330 | A1 | 9/2009 | Leinbach |
| 2010/0076333 | A9 | 3/2010 | Burton et al. |
| 2012/0002848 | A1 | 1/2012 | Hill |
| 2012/0046993 | A1 | 2/2012 | Hill |
| 2012/0289794 | A1 | 11/2012 | Jain et al. |
| 2013/0094722 | A1 | 4/2013 | Hill |
| 2013/0121591 | A1 | 5/2013 | Hill |
| 2014/0039857 | A1 | 2/2014 | Hill |
| 2014/0039975 | A1 | 2/2014 | Hill |
| 2014/0162225 | A1 | 6/2014 | Hill |

FOREIGN PATENT DOCUMENTS

| | | |
|---|---|---|
| EP | 1607842 | 12/2005 |
| JP | 05293172 | 11/1993 |
| JP | 07-329657 | 12/1995 |
| JP | 2002-000577 | 1/2002 |
| JP | 2002056500 | 2/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2003522580 | 7/2003 |
| JP | 2005084770 | 3/2005 |
| JP | 2006-323547 | 11/2006 |
| KR | 10-2000-0072489 | 12/2000 |
| KR | 10-2001-0104579 | 11/2001 |
| WO | 00/17824 | 3/2000 |
| WO | 01/97070 | 12/2001 |
| WO | 2004100765 | 11/2004 |
| WO | 2006005767 | 1/2006 |
| WO | 2007/019584 | 2/2007 |

OTHER PUBLICATIONS

Form PCT/ISA/220, PCT/US07/15019, "PCT Notification of Transmittal of The International Search Report and the Written Opinion of the International Searching Authority, or the Declaration," 1 pg.
Form PCT/ISA/210, PCT/US07/15019, "PCT International Search Report," 2 pgs.
Form PCT/ISA/237, PCT/US07/15019, "PCT Written Opinion of the International Searching Authority," 5 pgs.
Form PCT/IB/326, PCT/US07/015019, "Notification Concerning Transmittal of International Preliminary Report on Patentability."
Form PCT/IB/373, PCT/US07/15019, "International Preliminary Report on Patentability."
Form PCT/ISA/220, PCT/US07/14955, "PCT Notification of Transmittal of The International Search Report and the Written Opinion of the International Searching Authority, or the Declaration," 1 pg.
Form PCT/ISA/210, PCT/US07/14955, "PCT International Search Report," 2 pgs.
Form PCT/ISA/237, PCT/US07/14955, "PCT Written OpiniOn of the International Searching Authority," 6 pgs.
Form PCT/IB/326, PCT/US07/14955, "Notification Concerning Transmittal of International Preliminary Report on Patentability." 1 page.
Form PCT/IB/373, PCT/US07/14955, "International Preliminary Report on Patentability." 1 page.
Form PCT/ISA/220, PCT/US07/16796, "PCT Notification of Transmittal of The International Search Report and the Written Opinion of the International Searching Authority, or the Declaration," 1 pg.
Form PCT/ISA/210, PCT/US07/16796, "PCT International Search Report," 2 pgs.
Form PCT/ISA/237, PCT/US07/16796, "PCT Written Opinion of the International Searching Authority," 6 pgs.
Form PCT/IB/326, PCT/US07/16796, "Notification Concerning Transmittal of International Preliminary Report on Patentability." 1 page.
Form PCT/IB/373, PCT/US07/16796, "International Preliminary Report on Patentability." 1 page.
Form PCT/ISA/220, PCT/US06/31569, "PCT Notification of Transmittal of the International Search Report and the Written Opinion of the International Searching Authority, or the Declaration," 1 pg.
Form PCT/ISA/210, PCT/US06/31569, "PCT International Search Report," 3 pgs.
Form PCT/ISA/237, PCT/US06/31569, "PCT Written Opinion of the International Searching Authority," 6 pgs.
Form PCT/IB/326, PCT/US06/31569, "Notification Concerning Transmittal of International Preliminary Report on Patentability." 1 page.
Form PCT/IB/373, PCT/US06/31569, "International Preliminary Report on Patentability." 1 page.
Form PCT/ISA/220, PCT/US07/20714, "PCT Notification of Transmittal of The International Search Report and the Written Opinion of the International Searching Authority, or the Declaration," 1 pg.
Form PCT/ISA/210, PCT/US07/20714, "PCT International Search Report," 2 pgs.
Form PCT/ISA/237, PCT/US07/20714, "PCT Written Opinion of the International Searching Authority," 6 pgs.
Form PCT/IB/326, PCT/US07/20714, "Notification Concerning Transmittal of International Preliminary Report on Patentability." 1 page.
Form PCT/IB/373, PCT/US07/20714, "International Preliminary Report on Patentability." 1 page.
Form PCT/ISA/220, PCT/US07/17764, "PCT Notification of Transmittal of The International Search Report and the Written Opinion of the International Searching Authority, or the Declaration," 1 pg.
Form PCT/ISA/210, PCT/US07/17764, "PCT International Search Report," 2 pgs.
Form PCT/ISA/237, PCT/US07/17764, "PCT Written Opinion of the International Searching Authority," 7 pgs.
Form PCT/IB/326, PCT/US07/17764, "Notification Concerning Transmittal of International Preliminary Report on Patentability." 1 page.
Form PCT/IB/373, PCT/US07/17764, "International Preliminary Report on Patentability." 1 page.
Form PCT/ISA/220, PCT/US07/20713, "PCT Notification of Transmittal of The International Search Report and the Written Opinion of the International Searching Authority, or the Declaration," 1 pg.
Form PCT/ISA/210, PCT/US07/20713, "PCT International Search Report," 2 pgs.
Form PCT/ISA/237, PCT/US07/20713, "PCT Written Opinion of the International Searching Authority," 5 pgs.
Form PCT/IB/326, PCT/US07/20713, "Notification Concerning Transmittal of International Preliminary Report on Patentability." 1 page.
Form PCT/IB/373, PCT/US07/20713, "International Preliminary Report on Patentability." 1 page.
Form PCT/ISA/220, PCT/US08/09110, "PCT Notification of Transmittal of the International Search Report and the Written Opinion of the International Searching Authority, or the Declaration," 1 pg.
Form PCT/ISA/210, PCT/US08/09110, "PCT International Search Report," 3 pgs.
Form PCT/ISA/237, PCT/US08/09110, "PCT Written Opinion of the International Searching Authority," 4 pgs.
Form PCT/ISA/220, PCT/US08/75640, "PCT Notification of Transmittal of The International Search Report and the Written Opinion of the International Searching Authority, or the Declaration," 1 pg.
Form PCT/ISA/210, PCT/US08/75640, "PCT International Search Report," 2 pgs.

(56) References Cited

OTHER PUBLICATIONS

Form PCT/ISA/237, PCT/US08/75640, "PCT Written Opinion of the International Searching Authority," 3 pgs.
Form PCT/ISA/220, PCT/US08/78633, "PCT Notification of Transmittal of The International Search Report and the Written Opinion of the International Searching Authority, or the Declaration," 1 pg.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs.
Form PCT/ISA/220, PCT/US08/82147, "PCT Notification of Transmittal of The International Search Report and the Written Opinion of the International Searching Authority, or the Declaration," 1 pg.
Form PCT/ISA/210, PCT/US08/82147, "PCT International Search Report," 2 pgs.
Form PCT/ISA/237, PCT/US08/82147, "PCT Written Opinion of the International Searching Authority," 13 pgs.
Form PCT/ISA/220, PCT/US08/82149, "PCT Notification of Transmittal of The International Search Report and the Written Opinion of the International Searching Authority, or the Declaration," 1 pg.
Form PCT/ISA/210, PCT/US08/82149, "PCT International Search Report," 2 pgs.
Form PCT/ISA/237, PCT/US08/82149, "PCT Written Opinion of the International Searching Authority," 14 pgs.
Form PCT/ISA/220, PCT/US08/75651, "PCT Notification of Transmittal of The International Search Report and the Written Opinion of the International Searching Authority, or the Declaration," 1 pg.
Form PCT/ISA/210, PCT/US08/75651, "PCT International Search Report," 2 pgs.
Form PCT/ISA/237, PCT/US08/75651, "PCT Written Opinion of the International Searching Authority," 9 pgs.
Form PCT/ISA/220, PCT/US08/85723, "PCT Notification of Transmittal of The International Search Report and the Written Opinion of the International Searching Authority, or The Declaration," 1 pg.
Form PCT/ISA/210, PCT/US08/85723, "PCT International Search Report," 2 pgs.
Form PCT/ISA/237, PCT/US08/85723, "PCT Written Opinion of the International Searching Authority," 7 pgs.
Form PCT/ISA/220, PCT/US08/85203, "PCT Notification of Transmittal of The International Search Report and the Written Opinion of the International Searching Authority, or The Declaration," 1 pg.
Form PCT/ISA/210, PCT/US08/85203, "PCT International Search Report," 2 pgs.
Form PCT/ISA/237, PCT/US08/85203, "PCT Written Opinion of the International Searching Authority," 6 pgs.
Form PCT/ISA/220, PCT/US08/75649, "PCT Notification of Transmittal of The International Search Report and the Written Opinion of the International Searching Authority, or the Declaration," 1 pg.
Form PCT/ISA/210, PCT/US08/75649, "PCT International Search Report," 3 pgs.
Form PCT/ISA/237, PCT/US08/75649, "PCT Written Opinion of the International Searching Authority," 5 pgs.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., "Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalography Clinical Neurophysiology.

Mizuhara, H.,Wang LQ, Kobayashi, K., Yamaguchi, Y., (2004) A long range cortical network emerging with theta oscillation in mental task. Neuroreport 15(8): 1233-1238.
Seldon, G (1981) "Machines that Read Minds." Science Digest, October.
Willis, M. & Hodson, V.; Discover Your Child's Learning Style: Children Learn in Unique Ways-Here's the Key to Every Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry. Journal of Neuropsychiatry and Clinical Neurosciences. vol. 11(2): 190-208.
Decision of Rejection, English Language, issued by the State Intellectual Property Office of the P.R. China, in connection with Chinese application No. 201210063607.5, on Nov. 19, 2013, 10 pages.
Decision of Rejection, Chinese Language, issued by the State Intellectual Property Office of the P.R. China, in connection with Chinese application No. 201210063607.5, on Nov. 19, 2013, 6 pages.
Final Office Action, issued by the United States Patent and Trademark Office in connection with U.S. Appl. No. 13/553,515 on Jan. 9, 2014, 13 pages.
European office action, issued by the European Patent Office in connection with European patent application No. 07 852 430.3, on Feb. 6, 2013, 5 pages.
Final Decision of Rejection, English Language, issued by the Japanese Intellectual Property Office in connection with Japanese application No. 2009-552656, on Jan. 21, 2013, 3 pages.
Notice of Reason for Rejection, English Language, issued by the Japanese Intellectual Property Office in connection with Japanese application No. 2009-552660, on Mar. 13, 2013, 3 pages.
Notification of the Fourth Office Action, English Language, issued by the State Intellectual Property Office of the P.R. China, in connection with Chinese application No. 2006-80031159.3, on Oct. 18, 2012, 5 pages.
Advisory Action, issued by the United States Patent and Trademark Office in connection with U.S. Appl. No. 11/804,555, on Mar. 6, 2013, 3 pages.
Notice of Panel Decision from Pre-Appeal Brief Review, issued by the United States Patent and Trademark Office in connection with U.S. Appl. No. 11/804,555, on Mar. 25, 2013, 2 pages.
Notice for Reasons for Rejection, English Language, issued by the Intellectual Property Office of Japan, in connection with Japanese application No. 2009-552661, on Apr. 24, 2013, 2 pages.
Decision of Rejection, English Language, issued by the State Intellectual Property Office of the P.R. China, in connection with Chinese application No. 200780052879.2, on May 29, 2013, 11 pages.
Decision of Rejection, Chinese Language, issued by the State Intellectual Property Office of the P.R. China, in connection with Chinese application No. 200780052879.2, on May 29, 2013, 7 pages.
Final Office Action, issued by the United States Patent and Trademark Office in connection with U.S. Appl. No. 11/835,634 on Jun. 20, 2013, 23 pages.
First Office Action and Search Report, with English Language Version, issued by the State Intellectual Property Office of the Peoples' Republic of China, in connection with Chinese Patent Application No. 201210244954.8, on Jan. 2, 2014, 25 pages.
Notification of Reasons(s) for Rejection, issued by the Japanese Intellectual Property Office in connection with Japanese Patent Application No. 2012-152836, Jan. 14, 2014, 5 pages.
Notice of Allowance and Fee(s) Due, issued by the United States Patent and Trademark Office in connection with U.S. Appl. No. 11/845,993, on Feb. 19, 2014, 10 pages.

(56) References Cited

OTHER PUBLICATIONS

European Office Action, issued by the European Patent Office in connection with European Patent Application 07 852 430.3, on Feb. 3, 2014, 3 pages.
Office Action, issued by the United States Patent and Trademark Office in connection with U.S. Appl. No. 11/835,634, issued on Feb. 26, 2013, 24 pages.
Interrogative Statement, English Language, issued by the Intellectual Property Office of Japan, in connection with Japanese application No. 2009-552656, on Oct. 25, 2013, 4 pages.
European Office Action, issued by the European Patent Office in connection with European Patent Application No. 07796518.4, on Sep. 13, 2013, 7 pages.
European Office Action, issued by the European Patent Office in connection with European Patent Application No. 07838838.6, on Oct. 23, 2013, 4 pages.
Office Action, issued by the United States Patent and Trademark Office in connection with U.S. Appl. No. 13/553,515 on Jul. 17, 2013, 12 pages.
Notice of Allowance and Fee(s) Due, issued by the United States Patent and Trademark Office in connection with U.S. Appl. No. 11/804,555, on Mar. 3, 2014, 7 pages.
Notification of Reasons(s) for Rejection, issued by the Japanese Intellectual Property Office in connection with Japanese Patent Application No. 2009-552660 Jan. 21, 2014, 4 pages.
Notification of Grant of Patent Right for Invention, issued by the State Intellectual Property Office of the P.R. China, in connection with Chinese Patent Application No. 200780052869.9, on Aug. 31, 2012, 1 page.
Notification of the Third Office Action, issued by the State Intellectual Property Office of the P.R. China, in connection with Chinese Patent Application No. 200780052868.4, on Aug. 9, 2012, 7 pages.
Notification of the Second Office Action, issued by the State Intellectual Property Office of the P.R. China, in connection with Chinese Patent Application No. 200780052879.2, on May 4, 2012, 11 pages.
Notification of the Third Office Action, issued by the State Intellectual Property Office of the P.R. China, in connection with Chinese Patent Application No. 200680031159.3, on Mar. 28, 2012, 6 pages.
Notification of the Second Office Action, issued by the State Intellectual Property Office of the P.R. China, in connection with Chinese Patent Application No. 200680031159.3, on Oct. 19, 2011, 8 pages.
Notification of the Third Office Action, issued by the State Intellectual Property Office of the P.R. China, in connection with Chinese Patent Application No. 200780052879.2, on Dec. 31, 2012, 10 pages.
European Office Action, issued by the European Patent Office in connection with European Patent Application 07 838 838.6, on Sep. 5, 2012, 5 pages.
Supplemental European Search Report, issued by the European Patent Office in connection with European Patent Application No. 07796518.4, on Jul. 11, 2012, 8 pages.
European Office Action, issued by the European Patent Office in connection with European Patent Application No. 07 810 808.1, on Dec. 1, 2011, 6 pages.
Supplemental European Search Report, issued by the European Patent Office in connection with European Patent Appliation No. 06824810.3, on Nov. 22, 2011, 14 pages.
European Office Action, issued by the European Patent Office in connection with European Patent Application No. 07 852 430.3, on Mar. 6, 2012, 5 pages.
Supplemental European Search Report, issued by the European Patent Office in connection with European Patent Application No. 07811241.4, on Feb. 14, 2012, 6 pages.
European Office Action, issued by the European Patent Office in connection with European Patent Application No. 07 838 838.6, on Sep. 23, 2011, 4 pages.
Supplemental European Search Report, issued by the European Patent Office in connection with European Patent Application No. 06824810.3, on Nov. 3, 2011, 13 pages.
Supplemental European Search Report, issued by the European Patent Office in connection with European Patent Application No. 07796518.4, on Jul. 30, 2012, 9 pages.
Notification of Reason(s) for Rejection, issued by the Japanese Intellectual Property Office in connection with Japanese Patent Application No. 2009-552658, on Apr. 19, 2012, 2 pages.
Notification of Reason(s) for Rejection, issued by the Japanese Intellectual Property Office in connection with Japanese Patent Application No. 2009-552657, on May 2, 2012, 5 pages.
Notification of Reason(s) for Rejection, issued by the Japanese Intellectual Property Office in connection with Japanese Patent Application No. 2009-552656, on Mar. 30, 2012, 3 pages.
Notification of Reasons(s) for Rejection, issued by the Japanese Intellectual Property Office in connection with Japanese Patent Application No. 2008-529085, Nov. 29, 2011, 2 pages.
Notification of Reasons(s) for Rejection, issued by the Japanese Intellectual Property Office in connection with Japanese Patent Application No. 2009-552661, Nov. 13, 2012, 3 pages.
Notification of Reasons(s) for Rejection, issued by the Japanese Intellectual Property Office in connection with Japanese Patent Application No. 2009-552659, Nov. 16, 2012, 4 pages.
Notification of Reasons(s) for Rejection, issued by the Japanese Intellectual Property Office in connection with Japanese Patent Application No. 2009-552660, Nov. 16, 2012, 3 pages.
Notice of Allowance and Fee(s) Due, issued by the United States Patent and Trademark Office in connection with U.S. Appl. No. 11/804,517, on Mar. 21, 2012, 8 pages.
Final Rejection, issued by the United States Patent and Trademark Office in connection with U.S. Appl. No. 11/804,517, on Sep. 1, 2011, 11 pages.
Office Action, issued by the United States Patent and Trademark Office in connection with U.S. Appl. No. 11/804,517, on Feb. 3, 2011, 15 pages.
Final Rejection, issued by the United States Patent and Trademark Office in connection with U.S. Appl. No. 11/804,517, on Jun. 23, 2010, 14 pages.
Office Action, issued by the United States Patent and Trademark Office in connection with U.S. Appl. No. 11/804,517, on Sep. 17, 2009, 15 pages.
Office Action, issued by the United States Patent and Trademark Office in connection with U.S. Appl. No. 11/804,555, on Mar. 15, 2012, 15 pages.
Final Rejection, issued by the United States Patent and Trademark Office in connection with U.S. Appl. No. 11/804,555, on Oct. 9, 2012, 11 pages.
Final Rejection, issued by the United States Patent and Trademark Office in connection with U.S. Appl. No. 11/804,555, on Jul. 21, 2010, 14 pages.
Office Action, issued by the United States Patent and Trademark Office in connection with U.S. Appl. No. 11/804,555, on Oct. 1, 2009, 17 pages.
Office Action, issued by the United States Patent and Trademark Office in connection with U.S. Appl. No. 11/779,814, on Feb. 13, 2012, 19 pages.
Final Rejection, issued by the United States Patent and Trademark Office in connection with U.S. Appl. No. 11/779,814, on Jun. 28, 2012, 18 pages.
Final Rejection, issued by the United States Patent and Trademark Office in connection with U.S. Appl. No. 11/779,814, on Jun. 18, 2010, 24 pages.
Office Action, issued by the United States Patent and Trademark Office in connection with U.S. Appl. No. 11/779,814, on Oct. 5, 2009, 24 pages.
Final Rejection, issued by the United States Patent and Trademark Office in connection with U.S. Appl. No. 11/845,993, on Apr. 24, 2012, 8 pages.
Advisory Action, issued by the United States Patent and Trademark Office in connection with U.S. Appl. No. 11/845,993, on Jul. 20, 2012, 4 pages.
Office Action, issued by the United States Patent and Trademark Office in connection with U.S. Appl. No. 11/845,993, Aug. 4, 2011, 12 pages.

(56) References Cited

OTHER PUBLICATIONS

Final Rejection, issued by the United States Patent and Trademark Office in connection with U.S. Appl. No. 11/835,634, on Apr. 25, 2012, 23 pages.
Office Action, issued by the United States Patent and Trademark Office in connection with U.S. Appl. No. 11/835,634, on Sep. 1, 2011, 16 pages.
Final Rejection, issued by the United States Patent and Trademark Office in connection with U.S. Appl. No. 12/206,676, on Mar. 6, 2012, 9 pages.
Office Action, issued by the United States Patent and Trademark Office in connection with U.S. Appl. No. 12/206,676, on May 10, 2011, 9 pages.
Final Rejection, issued by the United States Patent and Trademark Office in connection with U.S. Appl. No. 12/206,702, on Jun. 3, 2010, 8 pages.
Office Action, issued by the United States Patent and Trademark Office in connection with U.S. Appl. No. 12/206,702, on May 28, 2009, 8 pages.
Final Rejection, issued by the United States Patent and Trademark Office in connection with U.S. Appl. No. 11/681,265, on Apr. 10, 2012, 18 pages.
Office Action, issued by the United States Patent and Trademark Office in connection with U.S. Appl. No. 11/681,265, on Jun. 21, 2011, 15 pages.
Restriction and/or Election Requirement, issued by the United States Patent and Trademark Office in connection with U.S. Appl. No. 11/846,068, on Feb. 21, 2012, 6 pages.
Office Action, issued by the United States Patent and Trademark Office in connection with U.S. Appl. No. 11/846,068, on Apr. 27, 2012, 9 pages.
Notice of Allowance and Fee(s) Due, issued by the United States Patent and Trademark Office in connection with U.S. Appl. No. 11/846,068, on Dec. 26, 2012, 9 pages.
Office Action, issued by the United States Patent and Trademark Office in connection with U.S. Appl. No. 12/835,714, on Jan. 22, 2013, 34 pages.
Adamic et al., "The political blogosphere and the 2004 U.S. election: Divided they blog," Proceedings WWW-2005 2nd Annual Workshop on the Weblogging Ecosystem, 2005, Chiba, Japan, 16 pages.
Adar et al., "Implicit structure and the dynamics of blogspace," Proceedings WWW-2004 Workshop on the Weblogging Ecosystem, 2004, New York, NY, 8 pages.
Aliod et al., "A Real World Implementation of Answer Extraction," Department of Computer Science, University of Zurich, Winterthurerstr. 190, CH-8057 Zurich, Switzerland, 6 pages.
Bishop, Mike, "ARROW Question/Answering Systems," Language Computer Corporation, 1999, 3 pages.
Bizrate, archived version of www.bizrate.com, Jan. 1999, 22 pages.
Blum, "Empirical Support for Winnow and Weighted-Majority Algorithms: Results on a Calendar Scheduling Domain," in Machine Learning, vol. 26, Kluwer Academic Publishers, Boston, USA, 1997, 19 pages.
Bournellis, Cynthia, "Tracking the hits on Web Sites," Communications International: vol. 22, Issue 9, London, Sep. 1995, 3 pages.
Chaum et al., "A Secure and Privacy-Protecting Protocol for Transmitting Personal Information Between Organizations," A.M. Odlyzko (Ed.): Advances in Cryptology, CRYPTO '86, LNCS 263, 1987, 51 pages.
Chaum, David L., "Untraceable Electronic Mail, Return Addresses, and Digital Pseudonymns," Communication of the ACM, vol. 24, No. 2, 1981, 5 pages.
Cohen, William W., "Data Integration using similarity joins and a word-based information representation language," ACM Transactions on Information Systems, vol. 18, No. 3, Jul. 2000, 34 pages.
Cohn et al., "Active Learning with Statistical Models," Journal of Artificial Intelligence Research 4, AI Access Foundation and Morgan Kaufmann Publishers, USA, 1996, 17 pages.

Dagan et al., "Mistake-Driven Learning in Text Categorization," in EMNLP '97, $2^{nd}$ Conference on Empirical Methods in Natural Language Processing, 1997, 9 pages.
Delahaye Group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.
Dialogic, www.dialogic.com as archived on May 12, 2000, 34 pages.
Dillon et al., "Marketing research in a Marketing Environment," Times Mirror/Mosby College, USA, 1987, 5 pages.
Ewatch, eWatch's archived web site retrieved from [URL: http://web.archive.org/web/19980522190526/wwww.ewatch.com] on Sep. 8, 2004, archived May 22, 1998, 50 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
Farber, Dave, "IP: eWatch and Cybersleuth," retrieved from [URL: http://www.interesting-people.org/archives/interesting-people/200006/msg00090.html] Jun. 29, 2000, 4 pages.
Freund et al., "Selective Sampling Using the Query by Committee Algorithm," Machine Learning 28 Kluwer Academic Publishers, The Netherlands, 1997, 36 pages.
Glance et al., "Analyzing online disussion for marketing intelligence," Proceedings WWW-2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug. 21-24, 2005, 10 pages.
Grefenstette et al., "Validating the Coverage of Lexical Resources for Affect Analysis and Automatically Classifying New Words along Semantic Axes," Chapter X, Mar. 3, 2004, 16 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Department of Computer Science and Engineering at Southern Methodist Universtity, 2000, 7 pages.
Harabagiu, Sanda M., "Mining Textual Answers with Knowledge-Based Indicators," Department of Computer Science and Engineering at Southern Methodist University, 2000, 5 pages.
Housley et al., "Internet X.509 Public Key Infrastructure Certificate and CRL Profile," Network Working Group Request for Comments: 2459, Jan. 1999, 121 pages.
Joachims, Thorsten, "Text Categorization with Support Vector Machines: Learning with Many Relevant Features," in Machine Learning: ECML-98, Tenth European Conference on Machine Learning, 1998, 7 pages.
Kahn et al., "Categorizing Web Documents using Competitive Learning: An ingredient of a Personal Adaptive Agent," IEEE 1997, 4 pages.
Katz, Boris, "From Sentence Processing to Information Access on the World Wide Web," MIT Artificial Intelligence Laboratory, Feb. 27, 1997, 20 pages.
Kleppner, "Advertising Procedure," 6th edition, 1977, Prentice-Hall, Inc., Englewood Cliffs, NJ, p. 492, 3 pages.
Kotler, "Marketing Management," PrenticeHall International Inc., Upper Saddle River, NJ, 1997, 10 pages.
Klimesch, "EEG alpha and theta oscillations reflect cognitive and memory performance: a review and analysis," Brain Research Reviews, vol. 29, 1999, 27 pages.
Lenz et al., "Question answering with Textual CBR," Department of Computer Science, Humboldt University Berlin, D-10099 Berlin, 1998, 12 pages.
Littlestone, Nick, "Learning Quickly When Irrelevant Attributes Abound: A New Linear-threshold Algorithm," in Machine Learning, vol. 2, Kluwer Academic Publishers, Boston, MA, 1988, 34 pages.
Marlow, "Audience, structure and authority in the weblog community," International Communication Association Conference, MIT Media Laboratory, New Orleans, LA 2004, 9 pages.

(56) References Cited

OTHER PUBLICATIONS

McCallum et al., "Text Classification by Bootstrapping with the Keywords, EM and Shrinkage," Just Research and Carnegie Mellon University, Pittsburgh, PA, circa 1999, 7 pages.
McLachlan et al., "The EM Algorithm and Extensions," John Wiley & Sons, Inc., New York, NY, 1997, 301 pages.
Moldovan et al., "LASSO: A Tool for Surfing the Answer Net," Department of Computer Science and Engineering at Southern Methodist University, 1999, 9 pages.
Nakashima et al., "Information Filtering for the Newspaper," IEEE 1997, 4 pages.
Nanno et al., "Automatic collection and monitoring of Japanese Weblogs," Proceedings WWW-2004 Workshop on the weblogging Ecosystem, 2004, New York, NY, 7 pages.
Netcurrent, NetCurrent's web site, http://web.archive.org/web/20000622024845/www.netcurrents.com, retrieved on Jan. 17, 2005, archived on Jun. 22, 2000 and Sep. 18, 2000, 17 pages.
Pang et al., "Thumbs up? Sentiment Classification using Machine Learning Techniques," in Proceedings of EMNLP 2002, 8 pages.
Reguly, "Caveat Emptor Rules on the Internet," The Globe and Mail (Canada): Report on Business Column, Apr. 10, 1999, 2 pages.
Reinartz, "Customer Lifetime Value Analysis: An Integrated Empirical Framework for Measurement and Explanation," dissertation: Apr. 1999, 68 pages.
Schmidt et al., "Frontal brain electrical activity (EEG) distinguishes valence and intensity of musical emotions," Cognition and Emotion, vol. 15 (4), Psychology Press Ltd, 2001, 14 pages.
Sammler, "Music and emotion: Electrophysiological correlates of the processing of pleasant and unpleasant music," Psychophysiology, vol. 44, Blackwell Publishing Inc., 2007, 12 pages.
Soderland et al., "Customer Satisfaction and Links to Customer Profitability: An Empirical Examination of the Association Between Attitudes and Behavior," SSE/EFI Working Paper Series in Business Administration, Jan. 1999, 22 pages.
Thomas, "International Marketing," International Textbook Company, Scranton, PA 1971, 3 pages.
Trigaux, Robert, "Cyberwar Erupts Over Free Speech Across Florida, Nation," Knight-Ridder Tribune Business News, May 29, 2000, 4 pages.
Tull et al., "Marketing Research Measurement and Method," MacMillan Publishing Company, New York, NY, 1984, 9 pages.
Voorhees, Ellen M., "The TREC-8 Question Answering Track Report," National Institute of Standards and Technology, 1999, 6 pages.
Wiebe et al., "Identifying Collocations for Recognizing Opinions," in proceedings of ACL/EACL '01 Workshop on Collocation, Toulouse, France, Apr. 9, 2001, 9 pages.
Word of Mouth Research Case Study, "The Trans Fat Issue, Analysis of online consumer conversation to understand how the Oreo lawsuit impacted word-of-mouth on trans fats," Aug. 16, 2004, 35 pages.
Yang, "An Evaluation of Statistical Approaches to Text Categorization," Information Retrieval 1 (1/2) Apr. 10, 1999, 12 pages.
Zagat, www.zagat.com, archived on Apr. 29, 1999, 33 pages.
Zagat, www.zagat.com, archived version of p. 34, Feb. 1999, 1 page.
Notification of the Second Office Action, issued by the State Intellectual Property Office of the P.R. China, in connection with Chinese Patent Application No. 201210063607.5, on Aug. 28, 2014, 9 pages.
Office Action, issued by the United States Patent and Trademark Office in connection with U.S. Appl. No. 12/206,676, on Oct. 2, 2014, 13 pages.
Notification of Reason(s) for Rejection, issued by the Japanese Intellectual Property Office in connection with Japanese Patent Application No. JP2009552656, on Aug. 27, 2014, 13 pages.
Coan, J. A, et al., "Voluntary Facial Expression and Hemispheric Asymmetry Over the Frontal Cortex," Psychophysiology, 38 (Nov. 2001), pp. 912-925, 14 pages.
European Office Action, issued by the European Patent Office in connection with European Patent Application No. 07838838.6 on Mar. 12, 2014, 3 pages.
Office Action, issued by the United States Patent and Trademark Office in connection with U.S. Appl. No. 13/553,515, on Jun. 20, 2014, 12 pages.
Notification of the Second Office Action, issued by the State Intellectual Property Office of the P.R. China, in connection with Chinese Patent Application No. 201210244954.8 on Jul. 10, 2014, 26 pages.
Summons to Attend Oral Proceedings Pursuant to Rule 115(1) EPC, issued by the European Patent Office in connection with European Patent Application No. 07796518A on Sep. 4, 2014, 7 pages.
Office Action, issued by the United States Patent and Trademark Office in connection with U.S. Appl. No. 11/681,265 on Dec. 2, 2014, 18 pages.
Notification of Grant of Patent Right for Invention, issued by the State Intellectual Property Office of the P.R. China, in connection with Chinese Patent Application No. 201210244954.8 on Dec. 16, 2014, 6 pages.
Notification of Reexamination, issued by the State Intellectual Property Office of the P.R. China, in connection with Chinese Patent Application No. 200780052879.2 on Feb. 4, 2015, 21 pages.
European Office Action, issued by the European Patent Office in connection with European Patent Application 07838838.6, on Feb. 23, 2015, 3 pages.
European Decision and Minutes, issued by the European Patent Office in connection with European Patent Application 07796518.4 on Mar. 12 and 13, 2015, 65 pages.
Notification on Grant of Patent Right for Invention, issued by the State Intellectual Property Office of the P.R. China, in connection with Chinese Patent Application No. 201210063607.5, on Mar. 31, 2015, 4 pages.
Final Rejection, issued by the United States Patent and Trademark Office in connection with U.S. Appl. No. 12/206,676, on Jun. 19, 2015, 16 pages.
Notification of Reexamination, issued by the State Intellectual Property Office of the P.R. China, in connection with Chinese Patent Application No. 200780052879.2, on Jul. 1, 2015, 12 pages.
Notice of Allowance and Fee(s) Due, issued by the United States Patent and Trademark Office in connection with U.S. Appl. No. 11/681,265, Jul. 17, 2015, 8 pages.

* cited by examiner

DEVICE AND METHOD FOR SENSING ELECTRICAL ACTIVITY IN TISSUE

RELATED APPLICATIONS

The present application claims the benefit of U.S. Provisional Application Ser. No. 60/713,899, filed on Sep. 2, 2005, which is incorporated herein by reference. In addition, the present application arises from a continuation of U.S. patent application Ser. No. 11/500,679, filed Aug. 8, 2006, which claims the benefit of U.S. Provisional Application Ser. No. 60/706,580, filed on Aug. 9, 2005, both of which are hereby incorporated by reference.

BACKGROUND

Devices used for sensing electrical activity in tissue have many uses in modern society. In particular modern electroencephalograms (EEGs) are used for measuring electrical activity in the brains of people for anesthesia monitoring, attention deficit disorder treatment, epilepsy prediction, and sleep monitoring, among other uses. Unfortunately, the complexity and cost of prior modern EEGs typically limits their use to clinics or other facilities where the device can be used on numerous people under the expert attention of a trained medical professional. Using the EEG on numerous people in a clinical setting helps to distribute the cost of the machine to the people which use it. EEGs can cost several thousand dollars.

Trained personnel are used for setting up and operating EEGs because of the complexities involved. Setting up prior EEGs involves preparing the skin of the person for connection of electrodes. The skin is typically prepared by shaving the hair from the area, sanding the skin to remove the outer surface and applying a conductive gel or liquid to the skin before attaching the electrode to the skin. Such extensive skin preparation is needed because contact resistance between the electrode and the skin must be reduced in order for prior EEGs to work properly. Contact resistance in these prior EEGs typically needs to be 20 k ohms or less.

Typical prior EEGs are subject to errors caused by electrical and magnetic noise from the environment surrounding the person. Errors are also caused by slight variations in internal components of the EEG and other sources, such as movement of the person during the operation of the EEG. Environmental noise can be caused by 60 Hz power in electrical wiring and lights in the area where the EEG is used, and other sources. Even the friction of any object moving through the air can cause noise from static electricity. Most or all prior EEGs have two electrodes are connected to the person's head and wires which are run from each of the electrodes to the EEG machine. The routing of the wires and the positions of the noise causing elements in the environment can cause significant errors in the measurements done by the EEG.

Measuring the electrical activity in the brain is difficult because the electrical signal being measured is many times smaller than the noise in the system. In many instances, the noise is on the order of a few volts or a few tens of volts while the electrical signal being measured is only in the microvolt range. This gives a signal-to-noise ratio of $10^6$.

Prior EEGs have used very precise differential amplifiers, such as instrumentation amplifiers, to measure the electrical signal. The amplifier is referenced to a common reference such as the leg of the user. Each of the two wires from the two electrodes on the person's head are connected to the inputs of the differential amplifier. The output of the differential amplifier is a voltage relative to the reference which is proportional to the difference in voltage between the two electrodes times a constant. The measurement in this case is very sensitive because the differential amplifier is finding a small difference, the brain signal, between two signals which are $10^6$ times as large. These are reasons why small variations in components, the routing of the wires and other factors cause significant errors in the measurement and why prior EEGs are expensive and hard to use.

Another problem with the prior EEGs is that the 60 Hz noise is amplified at the first stage which saturates the signals before they are subtracted. In prior EEGs, designers go to great lengths to design systems that balance or shield the noise to avoid saturation. Systems which use the principle of subtracting two large numbers in measuring a small number are prone to these kinds of problems.

The foregoing examples of the related art and limitations related therewith are intended to be illustrative and not exclusive. Other limitations of the related art will become apparent to those of skill in the art upon reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

A method is described for sensing electrical activity in tissue of a user. Electrical activity is detected from the tissue between a first point and a second point on skin of the user and a voltage signal is generated in response thereto which contains a signal of interest and undesired signals. The voltage signal is amplified to amplify the signal of interest and undesired signals without substantially amplifying the noise. The amplification results in an output signal.

Another method is disclosed for sensing electrical activity in tissue of a user in a noise environment that is subjected to electrical noise. A sensor electrode is connected to skin of the user at a first point. A reference electrode is connected to skin of the user at a second point which is in a spaced apart relationship to the first point to allow the sensor electrode to sense the electrical activity in the tissue at the first point relative to the second point. An amplifier is provided which is configured to amplify the electrical activity while substantially reducing the influence from the noise environment.

A sensor circuit is described for sensing electrical activity in tissue of a user and isolating and amplifying a signal of interest from the sensed electrical activity. The sensor circuit includes a sensor electrode for placing on skin of the user at a first point. A reference electrode for placing at a second point which is a distance away from the first point to allow the sensor electrode to sense the electrical activity and to produce a voltage signal relative to the second point which includes the signal of interest in response. An electronic module of the sensor circuit includes a power source with positive and negative source voltages and a source reference voltage which is electrically connected to the reference electrode. An amplifier is connected to receive power from the power source and to receive the voltage signal from the sensor electrode and the power source reference voltage. The amplifier produces an output signal which is proportional to the voltage signal relative to the power source reference voltage. A filter portion receives the output signal from the amplifier and attenuates electrical activity unrelated to the signal of interest while passing the signal of interest.

In addition to the exemplary aspects and embodiments described above, further aspects and embodiments will become apparent by reference to the drawings and by study of the following descriptions.

DETAILED DESCRIPTION

Figure 1:
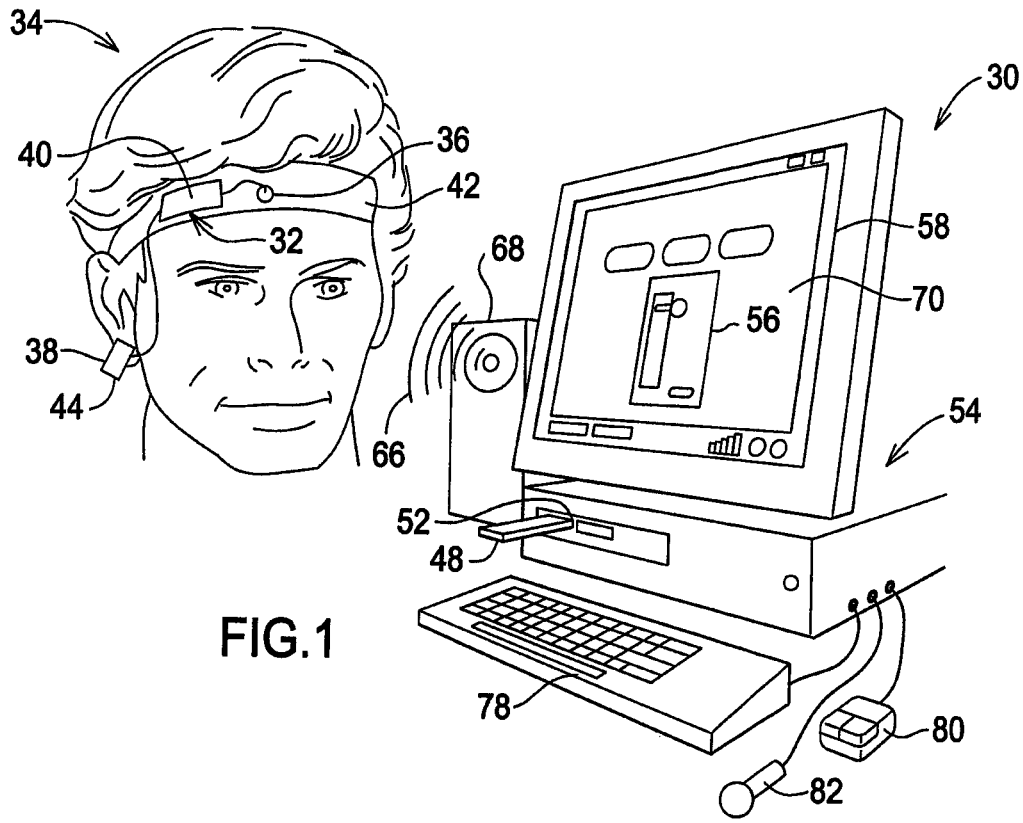
FIG. 1 is an illustration of a system which uses a sensor device which measures electrical activity to determine a present time emotional state of a user.

A system 30 which incorporates the present discussion is shown in FIG. 1. Exemplary system 30 includes a sensor device 32 which is connected to a user 34 for sensing and isolating a signal of interest from electrical activity in the user's pre-frontal lobe. The signal of interest has a measurable characteristic of electrical activity, or signal of interest, which relates to a present time emotional state (PTES) of user 34. PTES relates to the emotional state of the user at a given time. For instance, if the user is thinking about something that causes the user emotional distress, then the PTES is different than when the user is thinking about something which has a calming affect on the emotions of the user. In another example, when the user feels a limiting emotion regarding thoughts, then the PTES is different than when the user feels a state of release regarding those thoughts. Because of the relationship between the signal of interest and PTES, system 30 is able to determine a level of PTES experienced by user 34 by measuring the electrical activity and isolating a signal of interest from other electrical activity in the user's brain.

In the present example, sensor device 32 includes a sensor electrode 36 which is positioned at a first point and a reference electrode 38 which is positioned at a second point. The first and second points are placed in a spaced apart relationship while remaining in close proximity to one another. The points are preferably within about 8 inches of one another, and in one instance the points are about 4 inches apart. In the present example, sensor electrode 36 is positioned on the skin of the user's forehead and reference electrode 38 is connected to the user's ear. The reference electrode can also be attached to the user's forehead, which may include positioning the reference electrode over the ear of the user.

Sensor electrode 36 and reference electrode 38 are connected to an electronics module 40 of sensor device 32, which is positioned near the reference electrode 38 to that they are located substantially in the same noise environment. The electronics module 40 may be located at or above the temple of the user or in other locations where the electronics module 40 is in close proximity to the reference electrode 38. In the present example, a head band 42 or other mounting device holds sensor electrode 36 and electronics module 40 in place near the temple while a clip 44 holds reference electrode 38 to the user's ear. In one instance, the electronics module and reference electrode are positioned relative to one another such that they are capacitively coupled.

Sensor electrode 36 senses the electrical activity in the user's pre-frontal lobe and electronics module 40 isolates the signal of interest from the other electrical activity present and detected by the sensor electrode. Electronics module 40 includes a wireless transmitter 46, (FIG. 6), which transmits the signal of interest to a wireless receiver 48 over a wireless link 50. Wireless receiver 48, FIG. 1, receives the signal of interest from electronics module 40 and connects to a port 52 of a computer 54, or other device having a processor, with a port connector 53 to transfer the signal of interest from wireless receiver 48 to computer 54. Electronics module 40 includes an LED 55 (FIG. 6), and wireless receiver 48 includes an LED 57 which both illuminate when the wireless transmitter and the wireless receiver are powered.

In the present example, levels of PTES derived from the signal of interest are displayed in a meter 56, (FIGS. 1 and 2), on a computer screen 58 of computer 54. In this instance, computer 54, and screen 58 displaying meter 56 serve as an indicator. Levels of detail of meter 56 can be adjusted to to suit the user. Viewing meter 56 allows user 34 to determine their level of PTES at any particular time in a manner which is objective. The objective feedback obtained from meter 56 is used for guiding the user to improve their PTES and to determine levels of PTES related to particular memories or thoughts which can be brought up in the mind of user 34 when the user is exposed to certain stimuli. Meter 56 includes an indicator 60 which moves vertically up and down a numbered bar 62 to indicated the level of the user's PTES. Meter 56 also includes a minimum level indicator 64 which indicates a minimum level of PTES achieved over a certain period of time or during a session in which user 34 is exposed to stimuli from media material 66. Meter 56 can also include the user's maximum, minimum and average levels of release during a session. Levels of PTES may also be audibly communicated to the user, and in this instance, the computer and speaker serve as the indicator. The levels can also be indicated to the user by printing them on paper.

In another instance, different release levels relating to reaction to the same media material can be stored over time on a memory device. These different release levels can be displayed next to one another to inform the user on his or her progress in releasing the negative emotions related to the media material.

In system 30, media material 66 is used to expose user 34 to stimuli designed to cause user 34 to bring up particular thoughts or emotions which are related to a high level of PTES in the user. In the present example, media material 66 includes audio material that is played though computer 54 over a speaker 68. Media material 66 and meter 56 are integrated into a computer program 70 which runs on computer 54 and is displayed on computer screen 58. Media material 66 is controlled using on-screen buttons 72, in this instance. Computer program 70 also has other menu buttons 74 for manipulation of program functions and an indicator 76 which indicates connection strength of the wireless link 50. Program 70 is typically stored in memory of computer 54, this or another memory device can also contain a database for storing self reported journals and self-observed progress.

In some instances, program 70 may require a response or other input from user 34. In these and other circumstances, user 34 may interact with program 70 using any one or more suitable peripheral or input device, such as a keyboard 78, mouse 80 and/or microphone 82. For instance, mouse 80 may be used to select one of buttons 72 for controlling media material 66.

Media material 66 allows user 34 to interact with computer 54 for self or assisted inquiry. Media material 66 can be audio, visual, audio and visual, and/or can include written material files or other types of files which are played on or presented by computer 54. Media material 66 can be based on one or more processes, such as "The Release Technique" or others. In some instances, generic topics can be provided in the form of audio-video files presented in the form of pre-described exercises. These exercises can involve typical significant life issues or goals for most individuals, such as money, winning, relationships, and many other popular topics that allow the user to achieve a freedom state regarding these topics. The freedom state about the goal can be displayed when a very low level of PTES, (under some preset threshold) is achieved by the user regarding the goal. The release technique is used as an example in some instances; other processes may also be used with the technological approach described herein.

In one instance, media material 66 involving "The Release Technique" causes user 34 to bring up a limiting emotion or an emotion-laden experience type of PTES, which results in a disturbance in the nervous system of the user. The process then guides user 34 to normalize the nervous system or release the emotion while the user is focused on the perceived cause of the disturbance. When it is determined that the level of PTES, or release level in this instance, is below a preset threshold then the process is completed.

The signal of interest which relates to the release level PTES are brain waves or electrical activity in the pre-frontal lobe of the user's brain in the range of 4-12 Hz. These characteristic frequencies of electrical activity are in the Alpha and Theta bands. Alpha band activity is in the 8 to 12 Hz range and Theta band activity is in the 4 to 7 Hz range. A linear relationship between amplitudes of the Alpha and Theta bands is an indication of the release level. When user 34 is in a non-release state, the activity is predominantly in the Theta band and the Alpha band is diminished; and when user 34 is in a release state the activity is predominantly in the Alpha band and the energy in the Theta band is diminished.

When user 34 releases the emotion, totality of thoughts that remain in the subconscious mind is lowered in the brain as the disturbance is incrementally released from the mind. A high number of thoughts in the subconscious mind results in what is known as unhappiness or melancholy feelings, which are disturbances in the nervous system. A low number of thoughts in the subconscious mind results in what is known as happiness or joyful feelings, which results in a normalization or absence of disturbances in the nervous system.

Figure 3:
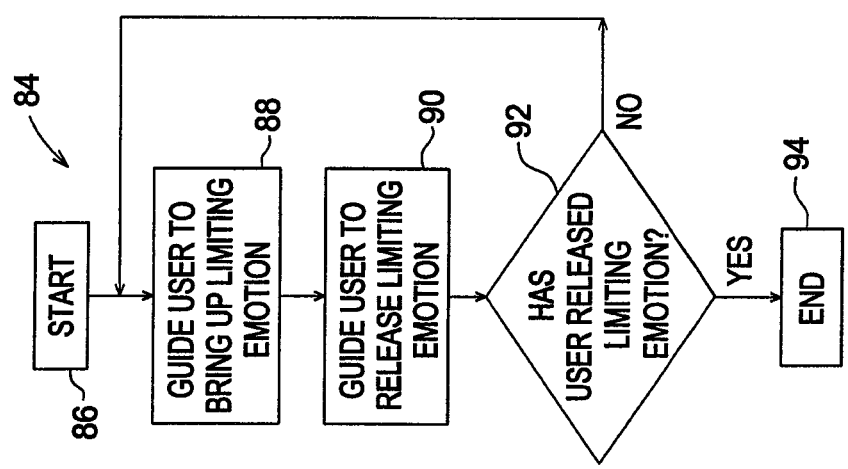
FIG. 3 is a diagram of one example in which the media material guides the user based on the present time emotional state of the user.

An exemplary method 84 which makes use of one or more self or assisted inquiry processes is shown in FIG. 3. Method 84 begins at a start 86 from which the method moves to a step 88. At step 88, program 70 uses stimuli in media material 66 to guide user 34 to bring up thoughts or subjects which causes an emotional disturbance in the PTES such as a limiting emotion. In the present example, media material 66 involves questions or statements directed to user 34 through speaker 68. In this and other instances, the computer can insert statements about goals or issue which were input by the user into the media material 66. For example, user 34 may input a goal statement using keyboard 78 and the computer may generate a voice which inserts the goal statement into the media material. In another example, the user may input the goal statement using microphone 82 and the computer may insert the goal statement into the media material.

Figure 2:
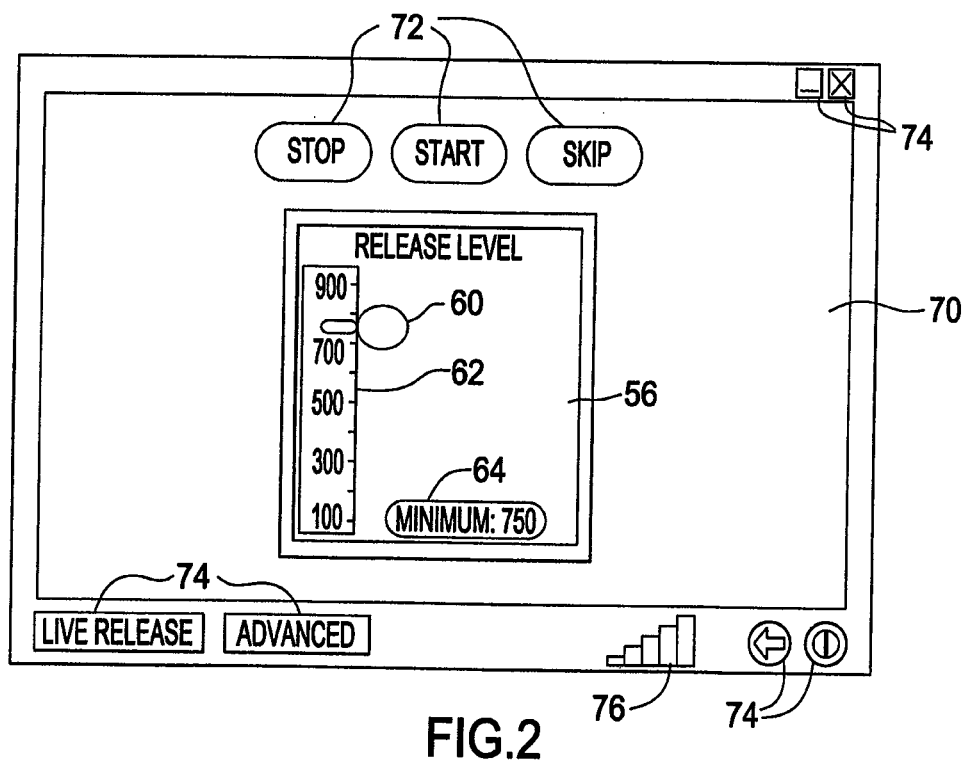
FIG. 2 is an illustration of a program which contains a display of a level of the present time emotional state of the user and has controls for media material used in guiding the user in relation to the present time emotional state of the user.

Method 84 then proceeds to step 90 where program 70 uses media material 66 to guide user 34 to release the limiting emotions while still focusing on the thought or subject which causes the limiting emotion. From step 90, the program proceeds to step 92 where a determination is made as to whether user 34 has released the limiting emotions. This determination is made using the signal of interest from sensor device 32. In the instance case, the level of release is indicated by the position of indicator 60 on bar 62 in meter 56, as shown in FIG. 2. If the meter indicates that user 34 has released the limiting emotions to an appropriate degree, such as below the preset threshold, then the determination at 92 is yes and method 84 proceeds to end at step 94. If the determination at 92 is that user 34 has not release the limiting emotions to an appropriate degree, then the determination at 92 is no, and method 84 returns to step 88 to again guide the user to bring up the thought or subject causing the limiting emotion. Method 84 can be continued as long as needed for user 34 to release the limiting emotions and achieve the freedom state. Processes can also include clean up sessions in which the user is guided by the media material to release many typical limiting emotions to assist the user in achieving a low thought frequency releasing the limiting emotions.

By observing meter 56 while attempting to release the limiting emotions, user 34 is able to correlate feelings with the release of limiting emotions. Repeating this process reinforces the correlation so that the user learns what it feels like to release and is able to release effectively with or without the meter 56 by having an increased releasing skill. A loop feature allows the user to click on a button to enter a loop session in which the releasing part of an exercise is repeated continuously. The levels of the user's PTES are indicated to the user and the levels are automatically recorded during these loop sessions for later review. Loop sessions provide a fast way in which to guide a user to let go of limiting emotions surrounding particular thoughts related to particular subjects. The loop session does not require the user to do anything between repetitions which allows them to maintain the desireable state of low thought activity, or the release state. Loop sessions can be included in any process for guiding the user to improve their PTES.

Computer 54 is also able to record release levels over time to a memory device to enable user 34 to review the releasing progress achieved during a recorded session. Other sessions can be reviewed along side of more recent sessions to illustrate the progress of the user's releasing ability by recalling the sessions from the memory device.

Figure 4:
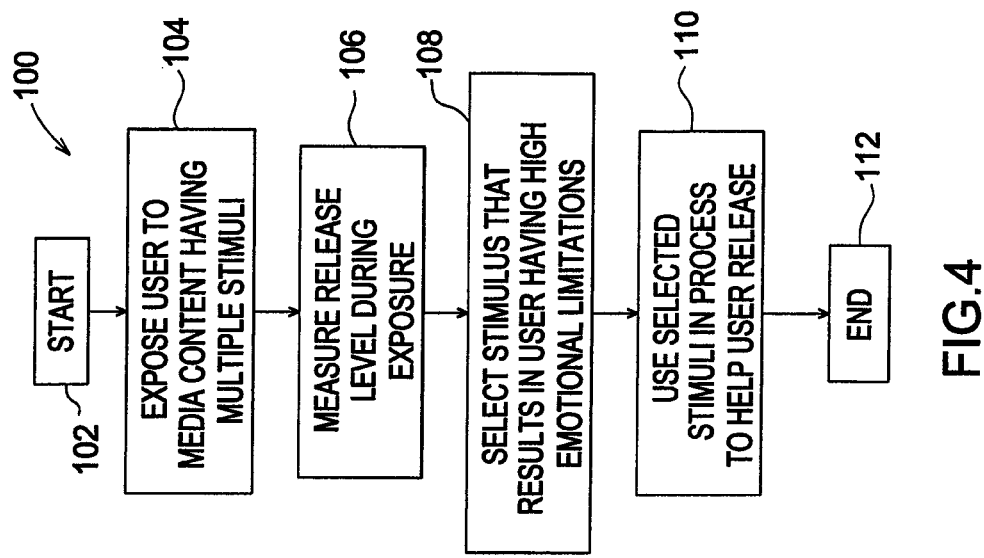
FIG. 4 is a diagram of another example in which the media material guides the user based on the present time emotional state of the user.

System 30 is also used for helping user 34 to determine what particular thoughts or subjects affect the user's PTES. An example of this use is a method 100, shown in FIG. 4. Method 100 begins at start 102 from which the method proceeds to step 104. At step 104, user 34 is exposed to a session of media content 42 which contains multiple stimuli that are presented to user 34 over time. Method 100 proceeds to step 106 where the levels of PTES of user 34 are determined during the session while the user is exposed to the multiple stimuli. Following step 106 method proceeds to step 108 where stimulus is selected from the media content 42 which resulted in negative affects on the PTES, such as high emotional limitations. Method 100 therefore identifies for the user areas which results in the negative affects on the PTES. Method 100 then proceeds to step 110 where the selected stimuli is used in a process to help the user release the negative emotions. Method 100 ends at step 112.

Figure 5:
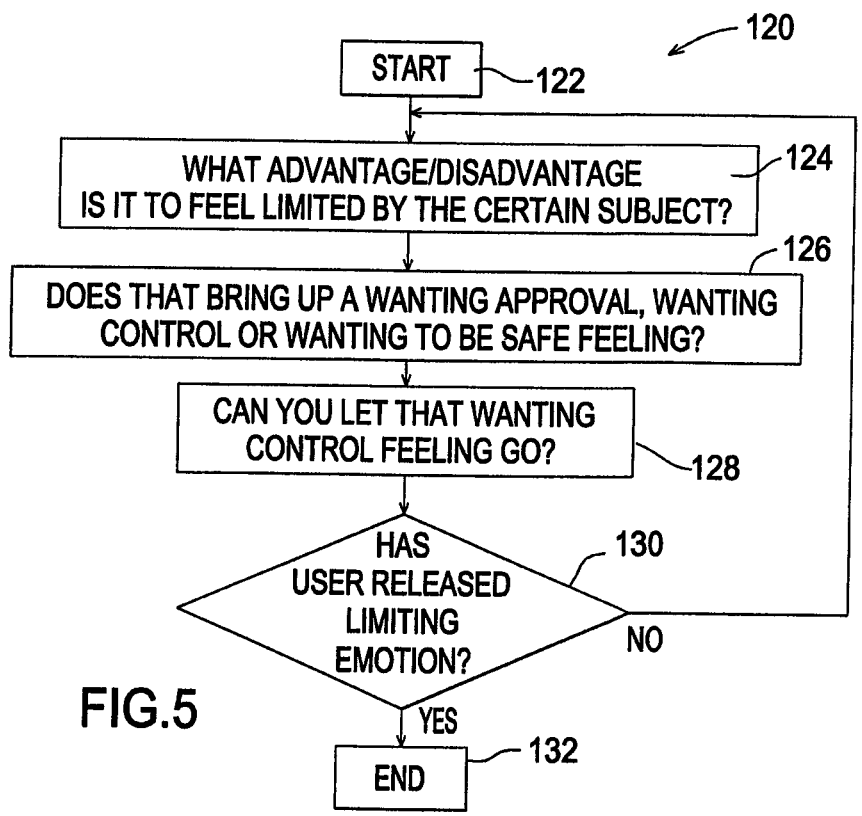
FIG. 5 is a diagram of yet another example in which the media material guides the user based on the present time emotional state of the user.

In one example, program 70 uses a method 120, FIG. 5, which includes a questioning pattern called "Advantages/Disadvantages." In this method, the media file asks user 34 several questions in sequence related to advantages/disadvantages of a "certain subject", which causes the user to experience negative emotions. Words or phrases of the "certain subject" can be entered into the computer by the user using one of the input devices, such as keyboard 78, mouse 80 and/or microphone 82 which allows the computer to insert the words or phrases into the questions. System 30 may also have goal documents that have the user's goal statements displayed along with the questioning patterns about the goal and release level data of the user regarding the goal. As an example, the user may have an issue which relates to control, such as a fear of being late for an airline flight. In this instance, the user would enter something like "fear of being late for a flight" as the "certain subject."

Series of questions related to advantages and disadvantage can be alternated until the state of release, or other PTES, is stabilized as low as possible, that is with the greatest amount of release. Method 120, shown in FIG. 5, starts at a start 122 from which it proceeds to step 124 where program 70 asks user 34 "What advantage/disadvantage is it to me to feel limited by the certain subject?" Program 70 then waits for feedback from the user through one of the input devices.

Program then proceeds to step 126 where program 70 asks user 34 "Does that bring up a wanting approval, wanting control or wanting to be safe feeling?" Program 70 waits for a response from user 34 from the input device and deciphers which one of the feelings the user responds with, such as "control feeling" for instance. Method 120 then proceeds to step 128 where program 70 questions the user based on the response given to step 128 by asking "Can you let that wanting control feeling go?" in this instance. At this point method 120 proceeds to step 130 where sensor device 32 determines the signal of interest to determine the release level of user 34. The release level is monitored and the media file stops playing when the release level has stabilized at its lowest point. At this time method 120 proceeds to step 132 and the session is complete. When the session is complete, user 34 will feel a sense of freedom regarding the certain subject. If some unwanted emotional residue is left, this same process can be repeated until complete freedom regarding the issue is realized by the user.

The above method is an example of "polarity releasing" in which an individual is guided to think about positives and negatives about a certain subject or particular issue, until the mind gives up on the negative emotions generated by the thoughts. There are other polarity releasing methods, such as "Likes/Dislikes" and other concepts and methods that help user's to achieve lower though frequency which may also be used along with a sensor device such as sensor device 32 for the purposes described herein.

Program 70 can store the history of responses to media on a memory device, and combine multiple iterations of responses to the same media in order to create a chart of improvement for user 34. Plotting these responses on the same chart using varying colors and dimensional effects demonstrates to user 34 the various PTES reactions over time to the same media stimulus, demonstrating improvement.

Program 70 can store reaction to live content as well. Live content can consist of listening to a person or audio in the same physical location, or listening to audio streaming over a telecommunications medium like telephone or the Internet, or text communications. Program 70 can send the PTES data from point-to-point using a communication medium like the Internet. With live content flowing in one direction, and PTES data flowing in the other, the deliverer of live content has a powerful new ability to react and change the content immediately, depending on the PTES data reaction of the individual. This deliverer may be a person or a web server application with the ability to understand and react to changing PTES.

Program 70 can detect the version of the electronic module 40 latently, based on the type of data and number of bytes being sent. This information is used to turn on and off various features in the program 70, depending on the feature's availability in the electronic module 40.

With certain types of computers and when certain types of wireless links are used, an incompatibility between wireless receiver 48 and computer 54 may occur. This incompatibility between an open host controller interface (OHCI) of the computer 54 and a universal host controller interface (UHCI) chip in the wireless receiver 48 causes a failure of communication. Program 70 has an ability to detect the symptom of this specific incompatibility and report it to the user. The detection scheme looks for a single response to a ping 'P' from the wireless receiver 48, and all future responses to a ping are ignored. Program 70 then displays a modal warning to the user suggesting workarounds for the incompatibility.

Program 70 detects the disconnecting of wireless link 50 by continually checking for the arrival of new data. If new data stops coming in, it assumes a wireless link failure, and automatically pauses the media being played and recording of PTES data. On detection of new data coming into the computer 54, the program 70 automatically resumes the media and recording.

Program 70 can create exercises and set goals for specific PTES levels. For example, it asks the user to set a target level of PTES and continues indefinitely until the user has reached that goal. Program 70 can also store reactions during numerous other activities. These other activities include but are not limited to telephone conversations, meetings, chores, meditation, and organizing. In addition, program 70 can allow users to customize their sessions by selecting audio, title, and length of session.

Other computing devices, which can include processor based computing devices, (not shown) can be used with sensor device 32 to play media material 66 and display or otherwise indicate the PTES. These devices may be connected to the sensor device 32 utilizing an integrated wireless receiver rather than the separate wireless receiver 48 which plugs into the port of the computer. These devices are more portable than computer 54 which allows the user to monitor the level PTES throughout the day or night which allows the user to liberate the subconscious mind more rapidly. These computing devices can include a camera with an audio recorder for storing and transmitting data to the receiver to store incidents of reactivity on a memory device for review at a later time. These computing devices can also upload reactivity incidents, intensity of these incidents and/or audio-video recordings of these incidents into computer 54 where the Attachment and Aversions process or other process can be used to permanently reduce or eliminate reactivity regarding these incidents.

Figure 6:
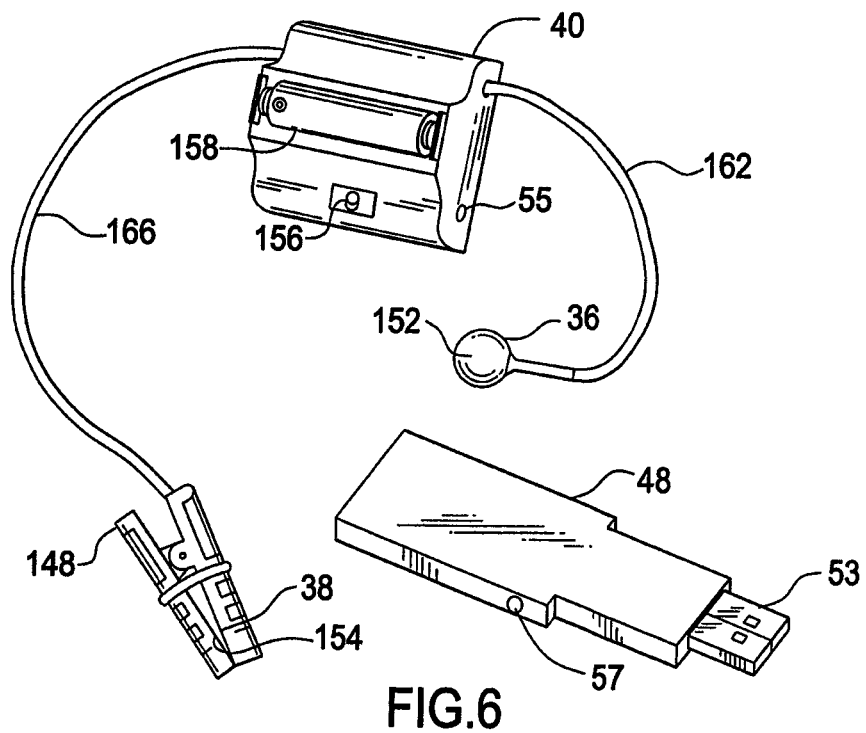
FIG. 6 is a perspective view of the sensor device shown in FIG. 1.
Figure 7:
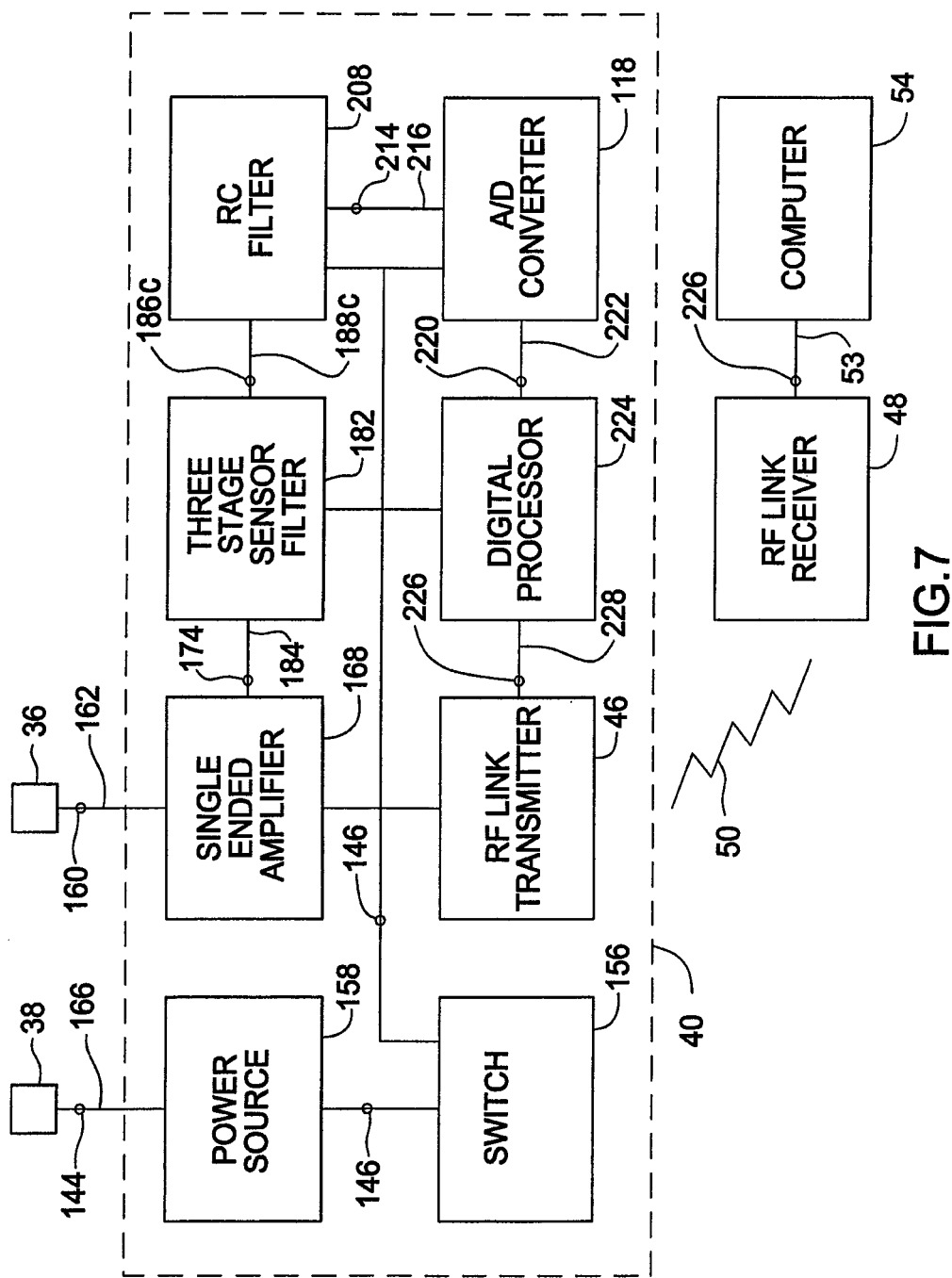
FIG. 7 is a block diagram of the sensor device and a computer shown in FIG. 1.

One example of sensor device 32 is shown in FIGS. 6 and 7. Sensor device 32 includes sensor electrode 36, reference electrode 38 and electronics module 40. The electronics module 40 amplifies the signal of interest by 1,000 to 100,000 times while at the same time insuring that 60 Hz noise is not amplified at any point. Electronics module 40 isolates the signal of interest from undesired electrical activity.

Sensor device 32 in the present example also includes wireless receiver 48 which receives the signal of interest from the electronics module over wireless link 50 and communicates the signal of interest to computer 54. In the present example, wireless link 50 uses radiofrequency energy; however other wireless technologies may also be used, such as infrared. Using a wireless connection eliminates the need for wires to be connected between the sensor device 32 and computer 54 which electrically isolates sensor device 32 from computer 54.

Reference electrode 38 is connected to a clip 148 which is used for attaching reference electrode 38 to an ear 150 of user 34, in the present example. Sensor electrode 36 includes a snap or other spring loaded device for attaching sensor electrode 36 to headband 42. Headband 42 also includes a pocket for housing electronics module 40 at a position at the user's temple. Headband 42 is one example of an elastic band which is used for holding the sensor electrode and/or the electronics module 40, another types of elastic bands which provide the same function could also be used, including having the elastic band form a portion of a hat.

Other types of mounting devices, in addition to the elastic bands, can also be used for holding the sensor electrode against the skin of the user. A holding force holding the sensor electrode against the skin of the user can be in the range of 1 to 4 oz. The holding force can be, for instance, 1.5 oz.

In another example of a mounting device involves a frame that is similar to an eyeglass frame, which holds the sensor electrode against the skin of the user. The frame can also be used for supporting electronics module 40. The frame is worn by user 34 in a way which is supported by the ears and bridge of the nose of the user, where the sensor electrode 36 contacts the skin of the user.

Sensor electrode 36 and reference electrode 38 include conductive surface 152 and 154, respectively, that are used for placing in contact with the skin of the user at points where the measurements are to be made. In the present example, the conductive surfaces are composed of a non-reactive material, such as copper, gold, conductive rubber or conductive plastic. Conductive surface 152 of sensor electrode 36 may have a surface area of approximately ½ square inch. The conductive surfaces 152 are used to directly contact the skin of the user without having to specially prepare the skin and without having to use a substance to reduce a contact resistance found between the skin and the conductive surfaces.

Sensor device 32 works with contact resistances as high as 500,000 ohms which allows the device to work with conductive surfaces in direct contact with skin that is not specially prepared. In contrast, special skin preparation and conductive gels or other substances are used with prior EEG electrodes to reduce the contact resistances to around 20,000 ohms or less. One consequence of dealing with higher contact resistance is that noise may be coupled into the measurement. The noise comes from lights and other equipment connected to 60 Hz power, and also from friction of any object moving through the air which creates static electricity. The amplitude of the noise is proportional to the distance between the electronics module 40 and the reference electrode 38. In the present example, by placing the electronics module over the temple area, right above the ear and connecting the reference electrode to the ear, the sensor device 32 does not pick up the noise, or is substantially unaffected by the noise. By positioning the electronics module in the same physical space with the reference electrode and capacitively coupling the electronics module with the reference electrode ensures that a local reference potential 144 in the electronics module and the ear are practically identical in potential. Reference electrode 38 is electrically connected to local reference potential 144 used in a power source 158 for the sensor device 32.

Power source 158 provides power 146 to electronic components in the module over power conductors. Power source 158 provides the sensor device 32 with reference potential 144 at 0 volts as well as positive and negative source voltages, −VCC and +VCC. Power source 158 makes use of a charge pump for generating the source voltages at a level which is suitable for the electronics module.

Power source is connected to the other components in the module 40 though a switch 156. Power source 158 can include a timer circuit which causes electronics module 40 to be powered for a certain time before power is disconnected. This feature conserves power for instances where user 34 accidentally leaves the power to electronics module 40 turned on. The power 146 is referenced locally to measurements and does not have any reference connection to an external ground system since sensor circuit 32 uses wireless link 50.

Sensor electrode 36 is placed in contact with the skin of the user at a point where the electrical activity in the brain is to be sensed or measured. Reference electrode 38 is placed in contact with the skin at a point a small distance away from the point where the sensor electrode is placed. In the present example, this distance is 4 inches, although the distance may be as much as about 8 inches. Longer lengths may add noise to the system since the amplitude of the noise is proportional to the distance between the electronics module and the reference electrode. Electronics module 40 is placed in close proximity to the reference electrode 38. This causes the electronics module 40 to be in the same of electrical and magnetic environment is the reference electrode 38 and electronics module 40 is connected capacitively and through mutual inductance to reference electrode 38. Reference electrode 38 and amplifier 168 are coupled together into the noise environment, and sensor electrode 36 measures the signal of interest a short distance away from the reference electrode to reduce or eliminate the influence of noise on sensor device 32. Reference electrode 38 is connected to the 0V in the power source 158 with a conductor 166.

Sensor electrode 36 senses electrical activity in the user's brain and generates a voltage signal 160 related thereto which is the potential of the electrical activity at the point where the sensor electrode 36 contacts the user's skin relative to the local reference potential 144. Voltage signal 160 is communicated from the electrode 36 to electronics module 40 over conductor 162. Conductors 162 and 166 are connected to electrodes 36 and 38 in such a way that there is no solder on conductive surfaces 152 and 154. Conductor 162 is as short as practical, and in the present example is approximately 3 inches long. When sensor device 32 is used, conductor 162 is held a distance away from user 34 so that conductor 162 does not couple signals to or from user 34. In the present example, conductor 162 is held at a distance of approximately ½" from user 34. No other wires, optical fibers or other types of extensions extend from the electronics module 40, other than the conductors 162 and 166 extending between module 40 and electrodes 36 and 38, since these types of structure tend to pick up electronic noise.

The electronics module 40 measures or determines electrical activity, which includes the signal of interest and other electrical activity unrelated to the signal of interest which is undesired. Electronics module 40 uses a single ended amplifier 168, (FIGS. 7 and 8), which is closely coupled to noise in the environment of the measurement with the reference electrode 38. The single ended amplifier 168 provides a gain of 2 for frequencies up to 12 Hz, which includes electrical activity in the Alpha and Theta bands, and a gain of less than 1 for frequencies 60 Hz and above, including harmonics of 60 Hz.

Figure 8:
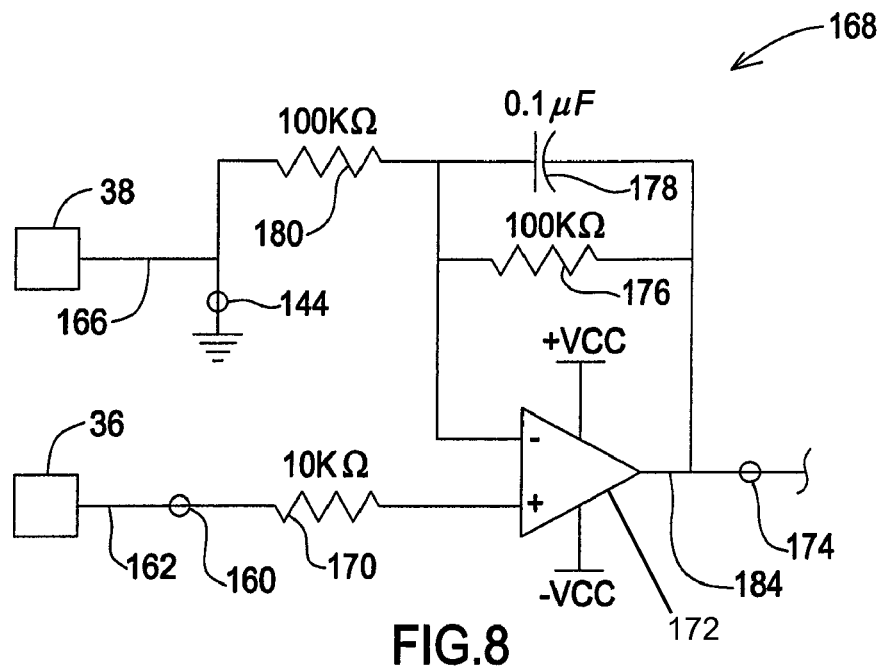
FIG. 8 is a circuit diagram of an amplifier used in the sensor device shown in FIG. 7.
Figure 11:
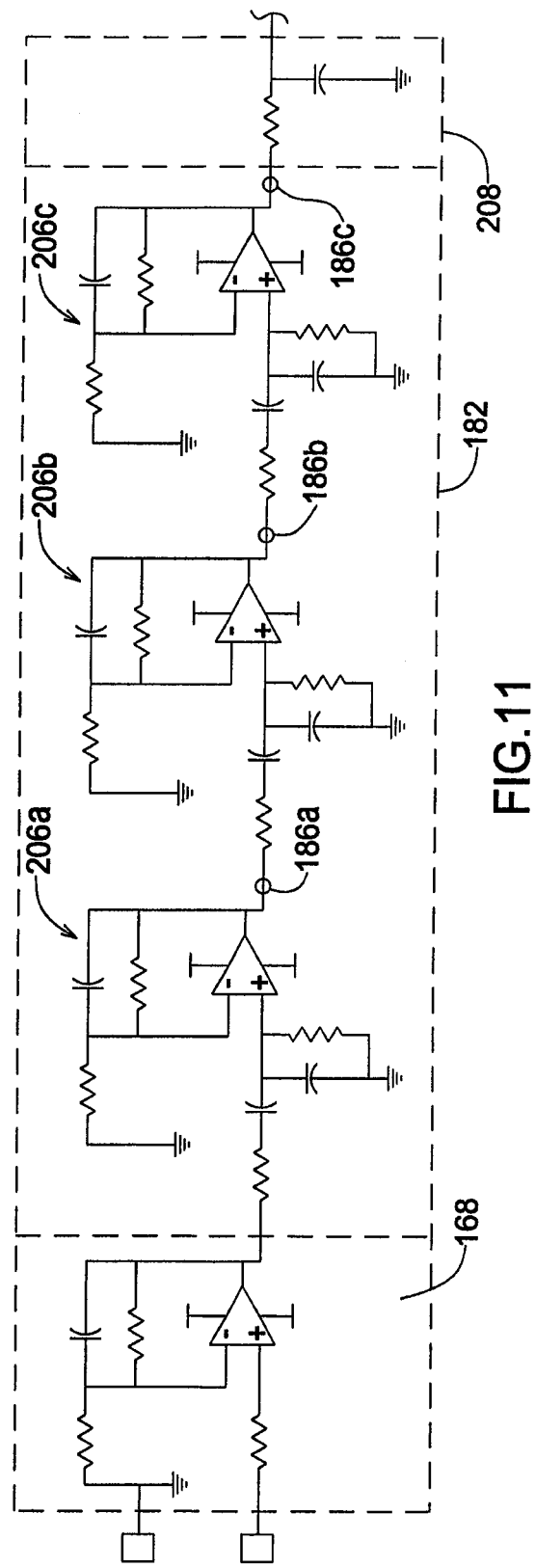
FIG. 11 is a circuit diagram of the amplifier, three filter stages and the RC filter shown in FIGS. 8, 9 and 10.

Amplifier 168, FIGS. 8 and 11, receives the voltage signal 160 from electrode 36 and power 146 from power source 158. Single ended amplifier 168 generates an output signal 174 which is proportional to voltage signal 160. Output signal 174 contains the signal of interest. In the present example, voltage signal 160 is supplied on conductor 162 to a resistor 170 which is connected to non-inverting input of high impedance, low power op amp 172. Output signal 174 is used as feedback to the inverting input of op amp 172 through resistor 176 and capacitor 178 which are connected in parallel. The inverting input of op amp 172 is also connected to reference voltage 144 through a resistor 180.

Amplifier 168 is connected to a three-stage sensor filter 182 with an output conductor 184 which carries output signal 174. The electrical activity or voltage signal 160 is amplified by each of the stages 168 and 182 while undesired signals, such as those 60 Hz and above, are attenuated by each of the stages. Three-stage sensor filter has three stages 206a, 206b and 206c each having the same design to provide a bandpass filter function which allows signals between 1.2 and 12 Hz to pass with a gain of 5 while attenuating signal lower and higher than these frequencies. The bandpass filter function allows signals in the Alpha and Theta bands to pass while attenuating noise such as 60 Hz and harmonics of the 60 Hz. The three stage sensor filter 182 removes offsets in the signal that are due to biases and offsets in the parts. Each of the three stages is connected to source voltage 146 and reference voltage 144. Each of the three stages generates an output signal 186a, 186b and 186c on an output conductor 188a, 186b and 188c, respectively.

Figure 9:
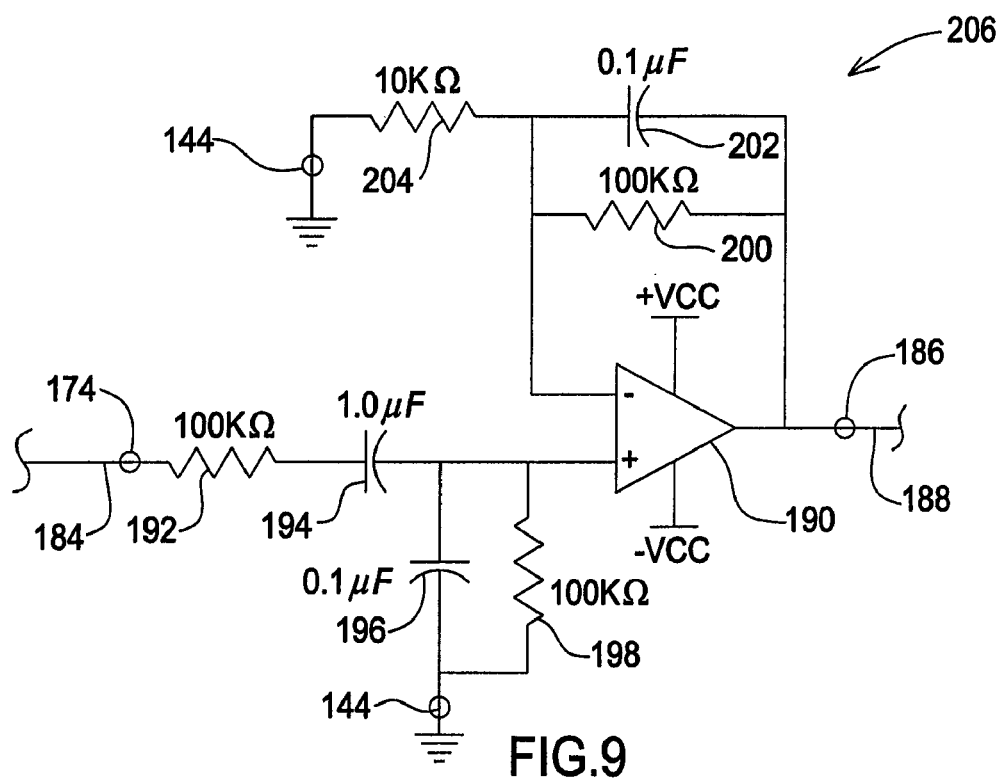
FIG. 9 is a circuit diagram of a filter stage used in the sensor device shown in FIG. 7.

In the first stage 206a, FIGS. 9 and 11, of three-stage sensor filter 182, output signal 174 is supplied to a non-inverting input of a first stage op-amp 190a through a resistor 192a and capacitor 194a. A capacitor 196a and another resistor 198a are connected between the non-inverting input and reference voltage 144. Feedback of the output signal 186a from the first stage is connected to the inverting input of op amp 190a through a resistor 200a and a capacitor 202a which are connected in parallel. The inverting input of op amp 190a is also connected to reference voltage 144 through resistor 204a.

Second and third stages 206b and 206c, respectively, are arranged in series with first stage 206a. First stage output signal 186a is supplied to second stage 206b through resistor 192b and capacitor 194b to the non-inverting input of op-amp 190b. Second stage output signal 186b is supplied to third stage 206c through resistor 192c and capacitor 194c. Resistor 198b and capacitor 196b are connected between the non-inverting input of op-amp 190b and reference potential 144, and resistor 198c and capacitor 196c are connected between the non-inverting input of op-amp 190c and reference potential 144. Feedback from output conductor 188b to the inverting input of op-amp 190b is through resistor 200b and capacitor 202b and the inverting input of op-amp 190b is also connected to reference potential 144 with resistor 204b. Feedback from output conductor 188c to the inverting input of op-amp 190c is through resistor 200c and capacitor 202c and the inverting input of op-amp 190c is also connected to reference potential 144 with resistor 204c.

Figure 10:
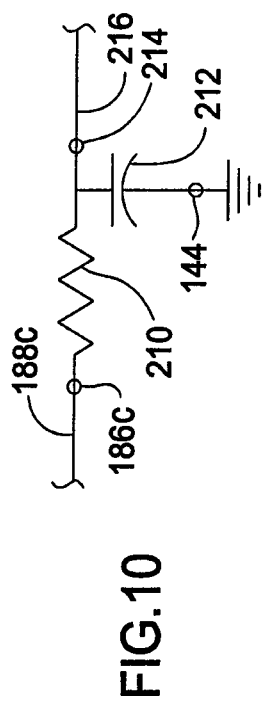
FIG. 10 is a circuit diagram of a resistor-capacitor RC filter used in the sensor device shown in FIG. 7.

Three stage sensor filter 182 is connected to an RC filter 208, FIGS. 10 and 11, with the output conductor 188c which carries the output signal 186c from third stage 206c of three stage sensor filter 182, FIG. 7. RC filter 208 includes a resistor 210 which is connected in series to an output conductor 216, and a capacitor 212 which connects between reference potential 144 and output conductor 216. RC filter serves as a low pass filter to further filter out frequencies above 12 Hz. RC filter 208 produces a filter signal 214 on output conductor 216. RC filter 208 is connected to an analog to digital (A/D) converter 218, FIG. 7.

A/D converter 218 converts the analog filter signal 214 from the RC filter to a digital signal 220 by sampling the analog filter signal 214 at a sample rate that is a multiple of 60 Hz. In the present example the sample rate is 9600 samples per second. Digital signal 220 is carried to a digital processor 224 on an output conductor 222.

Figure 12:
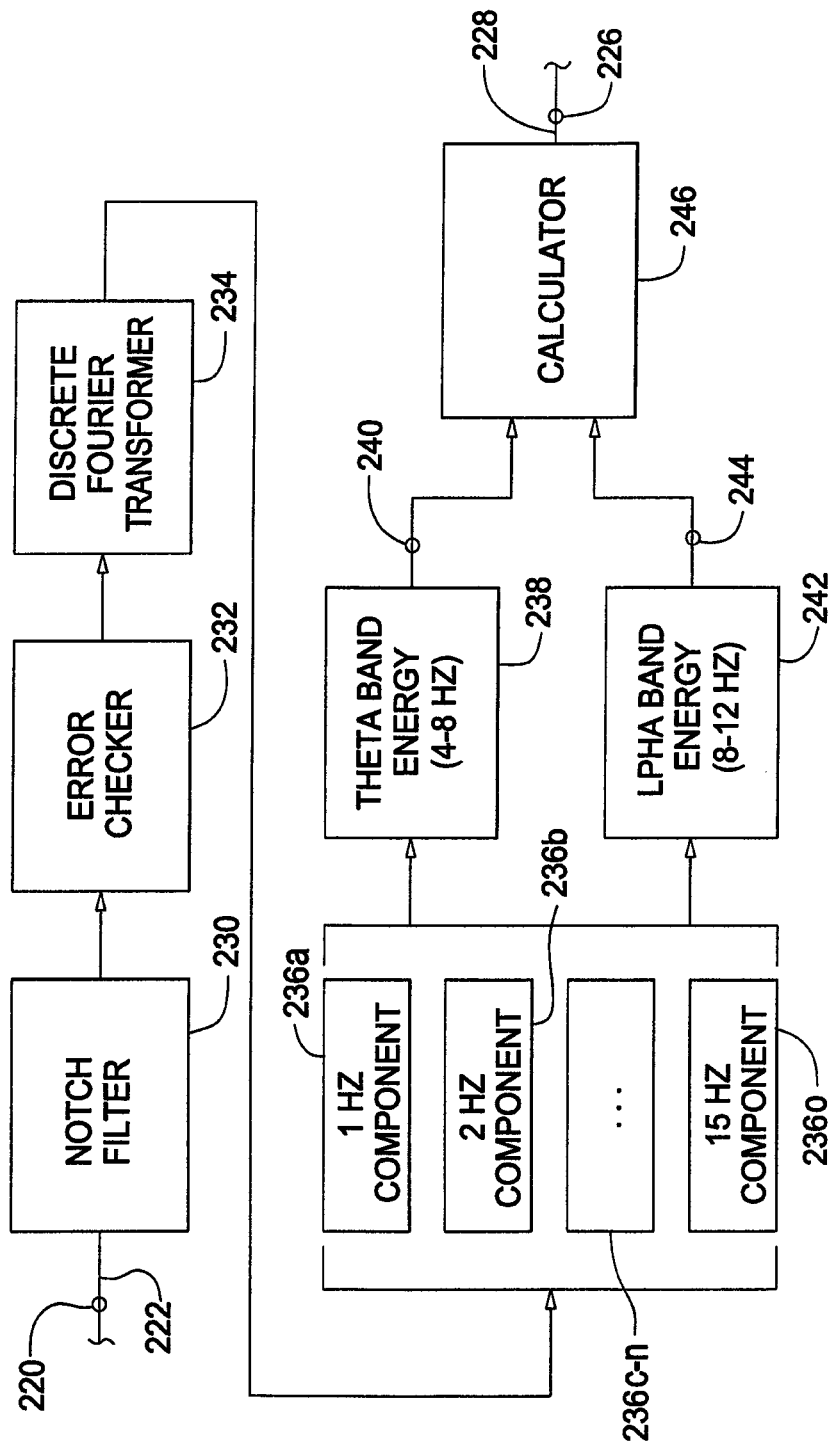
FIG. 12 is a block diagram of a digital processor of the sensor device shown in FIG. 7.

Digital processor 224, FIGS. 7 and 12 provides additional gain, removal of 60 Hz noise, and attenuation of high frequency data. Digital processor 224 many be implemented in software operating on a computing device. Digital processor 224 includes a notch filter 230, FIG. 12 which sums 160 data points of digital signal 220 at a time to produce a 60 Hz data stream that is free from any information at 60 Hz. Following notch filter 230 is an error checker 232. Error checker 232, removes data points that are out of range from the 60 Hz data stream. These out of range data points are either erroneous data or they are cause by some external source other than brain activity.

After error checker 232, digital processor 224 transforms the data stream using a discreet Fourier transformer 234. While prior EEG systems use band pass filters to select out the Alpha and Theta frequencies, among others, these filters are limited to processing and selecting out continuous periodic functions. By using a Fourier transform, digital processor 224 is able to identify randomly spaced events. Each event has energy in all frequencies, but shorter events will have more energy in higher frequencies and longer events will have more energy in lower frequencies. By looking at the difference between the energy in Alpha and Theta frequencies, the system is able to identify the predominance of longer or shorter events. The difference is then scaled by the total energy in the bands. This causes the output to be based on the type of energy and removes anything tied to amount of energy.

The Fourier transformer 234 creates a spectrum signal that separates the energy into bins 236a to 236o which each have a different width of frequency. In one example, the spectrum signal has 30 samples and separates the energy spectrum into 2 Hz wide bins; in another example, the spectrum signal has 60 samples and separates the bins into 1 Hz wide bins. Bins 236 are added to create energy signals in certain bands. In the present example, bins 236 between 4 and 8 Hz are passed to a summer 238 which sums these bins to create a Theta band energy signal 240; and bins between 8 and 12 Hz are passed to a summer 242 which sums these bins to create an Alpha band energy signal 244.

In the present example, the Alpha and Theta band energy signals 240 and 244 passed to a calculator 246 which calculates (Theta−Alpha)/Theta+Alpha) and produces an output signal 226 on a conductor 228 as a result.

Output signal 226, FIG. 7, is passed to wireless transmitter 46 which transmits the output signal 226 to wireless receiver 48 over wireless link 50. In the present example, output signal 226 is the signal of interest which is passed to computer 54 through port 52 and which is used by the computer to produce the PTES for display in meter 56.

Computer 54 may provide additional processing of output signal 226 in some instances. In the example using the Release Technique, the computer 54 manipulates output signal 226 to determine relative amounts of Alpha and Theta band signals in the output signal to determine levels of release experienced by user 34.

A sensor device utilizing the above described principles and feature can be used for determining electrical activity in other tissue of the user in addition to the brain tissue just described, such as electrical activity in muscle and heart tissue. In these instances, the sensor electrode is positioned on the skin at the point where the electrical activity is to be measured and the reference electrode and electronics module are positioned nearby with the reference electrode attached to a point near the sensor electrode. The electronics module, in these instances, includes amplification and filtering to isolate the frequencies of the muscle or heart electrical activity while filtering out other frequencies.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method comprising:
    detecting electrical activity from a tissue of a user via a sensor of a headpiece worn by the user, the sensor including:
        a sensor electrode to contact a first point on skin of the user;
        a reference electrode to contact a second point on the skin of the user, the contact between the reference electrode and the skin of the user to cause a contact resistance between a surface of the reference electrode and the skin of the user; and
        an electronics module positioned proximate the reference electrode to reduce noise, a local reference potential in the electronics module and a potential of the second point on the skin being approximately equal to allow the surface of the reference electrode to be in direct contact with the skin of the user at the second point without having to prepare the skin or use a material that decreases the contact resistance, the electrical activity represented by a voltage signal including a signal of interest, undesired signals, and noise, the electronics module including:
            an amplifier to (1) amplify the signal of interest and the undesired signals within a first frequency range while (2) filtering the noise occurring in a second frequency range, which includes frequencies higher than the first frequency range, prior to transmitting the amplified signal of interest and undesired signals to one or more filters; and
    transforming, with a processor and a Fourier transform, the signal of interest to form an output signal.

2. A method as defined in claim 1, wherein the amplifier is to amplify the signal of interest and the undesired signals by using the local reference potential of the electronics module, and connecting the second point directly to the local reference potential.

3. A method as defined in claim 1, wherein the amplifier is to amplify the signal of interest at the electronics module by using the local reference potential and source voltages, and positioning the electronics module in a region of the headpiece adjacent to the second point so as to electrically couple the local reference potential and source voltages to the second point.

4. A method as defined in claim 1, wherein the amplifier is to amplify the signal of interest at the electronics module and detecting the electrical activity includes using conductors extending from the electronics module to the sensor and reference electrodes at the first and second points, and electrically isolating the electronics module by keeping the electronics module free of wires, optical fibers or other extensions other than the conductors extending to the sensor and reference electrodes.

5. A method as defined in claim 1 further including filtering an output signal of the amplifier with the electronics module to attenuate the undesired signals and to isolate the signal of interest from the undesired signals.

6. A method as defined in claim 5 further including communicating the signal of interest to a computing device.

7. A method as defined in claim 6, wherein the computing device is to display information relating to the signal of interest.

8. A method as defined in claim 6, wherein the computing device is to produce audio related to the signal of interest.

9. A method as defined in claim 5, wherein the signal of interest relates to electrical activity in brain tissue of the user.

10. A method as defined in claim 5, wherein the signal of interest relates to electrical activity in muscle tissue of the user.

11. A method as defined in claim 5, wherein the signal of interest relates to electrical activity in heart tissue of the user.

12. A method as defined in claim 5, wherein filtering the output signal of the amplifier attenuates undesired signals below about 4 Hz and above about 12 Hz.

13. A method as defined in claim 5, wherein the signal of interest includes Alpha and Theta band brain waves.

14. A method as defined in claim 1, wherein the second point is on an ear of the user.

15. A method as defined in claim 1, wherein the second point is approximately 4 inches from the first point.

16. A method as defined in claim 1, wherein the second point is on a forehead of the user.

17. A method as defined in claim 1, wherein the second point is within approximately 8 inches of the first point.

18. A method as defined in claim 1, wherein the undesired signals include noise signals caused by environmental noise.

19. A method as defined in claim 1, wherein a contact resistance of the sensor electrode and the reference electrode can be as high as 500,000 ohms.

20. A method as defined in claim 1 further including positioning the electronics module with the processor at a temple of the user and positioning the reference electrode at an ear of the user.

21. A method as defined in claim 20, wherein the processor and reference electrode are to be positioned at the right temple and ear of the user.

22. A method as defined in claim 1 further including:
    isolating the signal of interest from the undesired signals by filtering the output signal.

23. A method as defined in claim 1, wherein the processor is to convert the output signal from analog to digital, wherein the output signal is converted at a rate that is a multiple of 60 Hz.

24. A method as defined in claim 1 further including testing the output signal for data that is inconsistent with EEG data, and removing the inconsistent data from the output signal.

25. A method as defined in claim 1 further including transforming the output signal using the Fourier Transform to determine an energy spectrum signal based on an energy spectrum of the output signal.

26. A method as defined in claim 25 further including dividing the energy spectrum signal into groups of 60 samples and separating the energy spectrum into 1 Hz wide bins.

27. A method as defined in claim 25 further including dividing the energy spectrum signal into groups of 30 samples and separating the energy spectrum into 2 Hz wide bins.

28. A method as defined in claim 25 further including dividing the energy spectrum signal into groups of samples and separating the energy spectrum into bins which each represent energy in a certain range of frequencies, and summing energy in bins that have about 4-8 Hz to create a Theta band energy signal.

29. A method as defined in claim 28 further including summing energy in bins that have about 8-12 Hz to create an Alpha band energy signal.

30. A method as defined in claim 29 further including generating the signal of interest by determining a ratio of the Alpha and Theta band energy signals.

31. A method comprising:
  detecting electrical activity from a tissue of a user via a sensor of a headpiece worn by the user, the sensor including an electronics module, a sensor electrode and a reference electrode, the sensor electrode is to contact a first point on skin of the user and the reference electrode is to contact a second point on the skin of the user, the contact between the reference electrode and the skin of the user to cause a contact resistance between a surface of the reference electrode and the skin of the user, the electronics module being positioned proximate the reference electrode to reduce noise, a local reference potential in the electronics module and a potential of the second point on the skin being approximately equal to allow the surface of the reference electrode to be in direct contact with the skin of the user at the second point without having to prepare the skin or use a material that decreases the contact resistance, the electrical activity represented by a voltage signal including a signal of interest and undesired signals;
  transforming, with a processor, the voltage signal using a Fourier Transform to determine an energy spectrum signal based on an energy spectrum of the voltage signal;
  dividing the energy spectrum signal into groups of samples and separating the energy spectrum into bins that represent energy in a certain range of frequencies;
  summing energy in bins that have about 4-8 Hz to create a Theta band energy signal;
  summing energy in bins that have about 8-12 Hz to create an Alpha band energy signal; and
  generating the signal of interest by determining a ratio of the Alpha and Theta band energy signals, wherein the ratio includes (Theta signal−Alpha signal)/(Theta signal+Alpha signal).

32. A method as defined in claim 1 further including:
  sampling the output signal for a certain number of samples in each $1/60^{th}$ of a second; and
  summing the samples from each $1/60^{th}$ of a second to create a processed signal with no 60 Hz interference.

33. A method as defined in claim 1, wherein the sensor electrode is electrically coupled to a first input of the amplifier, the reference electrode is electrically coupled to a second input of the amplifier, and an output of the amplifier is electrically coupled to the second input of the amplifier via a low pass filter.

34. A method as defined in claim 33, wherein the reference electrode is in circuit with the local reference potential in the electronics module.

35. A method as defined in claim 34, wherein a signal path of the sensor electrode to the first input is electrically isolated from a signal path of the reference electrode to the second input.

36. A method as defined in claim 1, wherein the amplifier is a low pass operational amplifier.

37. A method as defined in claim 36, wherein the noise includes signals above about 60 Hz.

38. A method as defined in claim 1, wherein the electronics module further includes a filter electrically coupled to an output of the amplifier, wherein the filter is to isolate the signal of interest and further attenuate the noise.

39. A method as defined in claim 38, wherein the amplifier is a first amplifier, and the filter includes a second amplifier, and wherein the output of the first amplifier is electrically coupled to a first input of the second amplifier, and an output of the second filter is electrically coupled to a second input of the second filter via a low pass filter.

40. A method as defined in claim 1, wherein the electronics module includes a converter to convert the signal of interest into digital form prior to transforming the signal of interest with the Fourier transform.

41. A method as defined in claim 1, wherein the electrical activity is from a muscle and a heart of the user.

* * * * *